(12) United States Patent
Song et al.

(10) Patent No.: US 9,999,704 B2
(45) Date of Patent: Jun. 19, 2018

(54) AMPHIPHILIC DEGRADABLE POLYMERS FOR IMMOBILIZATION AND SUSTAINED DELIVERY OF BIOMOLECULES

(71) Applicant: University of Massachusetts, Boston, MA (US)

(72) Inventors: Jie Song, Shrewsbury, MA (US); Jing Zhang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days. days.

(21) Appl. No.: 15/121,734

(22) PCT Filed: Feb. 26, 2015

(86) PCT No.: PCT/US2015/017640
§ 371 (c)(1),
(2) Date: Aug. 25, 2016

(87) PCT Pub. No.: WO2015/130877
PCT Pub. Date: Sep. 3, 2015

(65) Prior Publication Data
US 2017/0014547 A1   Jan. 19, 2017

Related U.S. Application Data

(60) Provisional application No. 61/945,117, filed on Feb. 26, 2014.

(51) Int. Cl.
| | |
|---|---|
| *A61L 27/00* | (2006.01) |
| *A61L 27/18* | (2006.01) |
| *A61L 27/54* | (2006.01) |
| *A61L 27/56* | (2006.01) |
| *A61L 31/06* | (2006.01) |
| *A61L 31/14* | (2006.01) |
| *A61L 31/16* | (2006.01) |
| *C08G 63/664* | (2006.01) |
| *A61L 27/58* | (2006.01) |
| *A61L 31/10* | (2006.01) |
| *C08G 63/82* | (2006.01) |

(52) U.S. Cl.
CPC ............. *A61L 27/18* (2013.01); *A61L 27/54* (2013.01); *A61L 27/56* (2013.01); *A61L 27/58* (2013.01); *A61L 31/06* (2013.01); *A61L 31/10* (2013.01); *A61L 31/146* (2013.01); *A61L 31/148* (2013.01); *A61L 31/16* (2013.01); *C08G 63/664* (2013.01); *C08G 63/823* (2013.01); *A61L 2300/22* (2013.01); *A61L 2300/414* (2013.01); *C08G 2230/00* (2013.01)

(58) Field of Classification Search
None
See application file for complete search history.

(56) References Cited

U.S. PATENT DOCUMENTS

| | | | | |
|---|---|---|---|---|
| 2006/0165987 A1* | 7/2006 | Hildgen | ............... | A61K 9/5153 428/402.2 |
| 2006/0246121 A1* | 11/2006 | Ma | ........................ | A61K 9/0024 424/443 |
| 2008/0317816 A1* | 12/2008 | Ma | ......................... | A61K 9/146 424/426 |
| 2009/0092582 A1* | 4/2009 | Bogin | .................... | C07K 14/56 424/85.5 |
| 2009/0281068 A1* | 11/2009 | Moller | ................. | A61K 9/0024 514/152 |
| 2012/0093717 A1* | 4/2012 | Mauck | .................... | A61L 27/18 424/1.11 |

* cited by examiner

*Primary Examiner* — Robert A Wax
*Assistant Examiner* — Quanglong N Truong
(74) *Attorney, Agent, or Firm* — Milstein Zhang & Wu LLC

(57) ABSTRACT

The invention provides a novel approach to controlled delivery of biomolecules (e.g., lipids and proteins) by employing novel amphiphilic polymers that are effective delivery vehicles. These unique amphiphilic polymers may be employed as controlled delivery vehicles or tissue engineering scaffolds wherein the delivery of lipophilic or amphiphilic bioactive molecules can be achieved. An amphiphilic biodegradable polymer platform is disclosed herein for the stable encapsulation and sustained release of biomolecules, such as S1P.

20 Claims, 12 Drawing Sheets

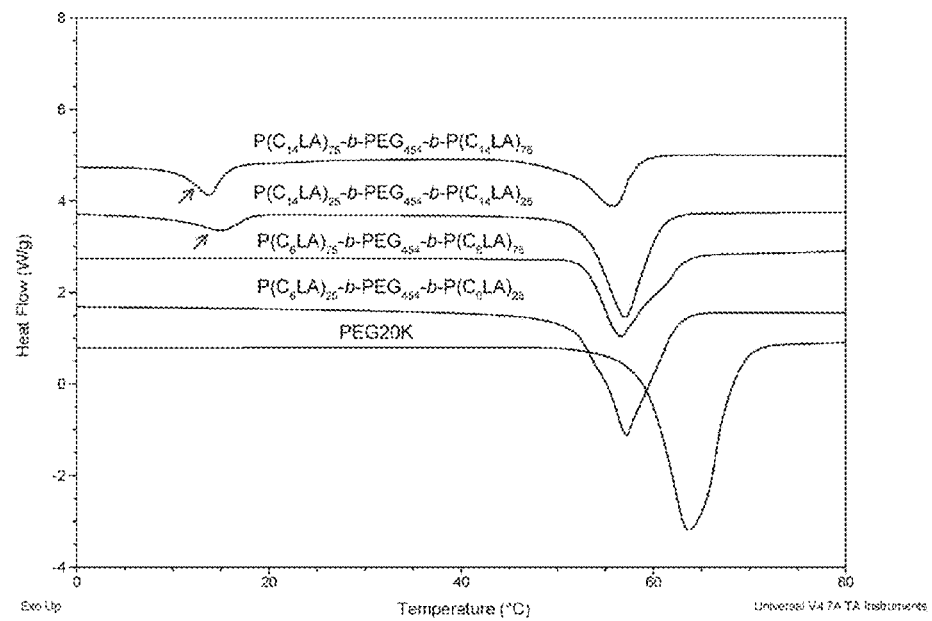
FIG. 8. DSC spectra (second heating cycle) of PEG20K vs. the C14- and C6-alkylated triblock copolymers.

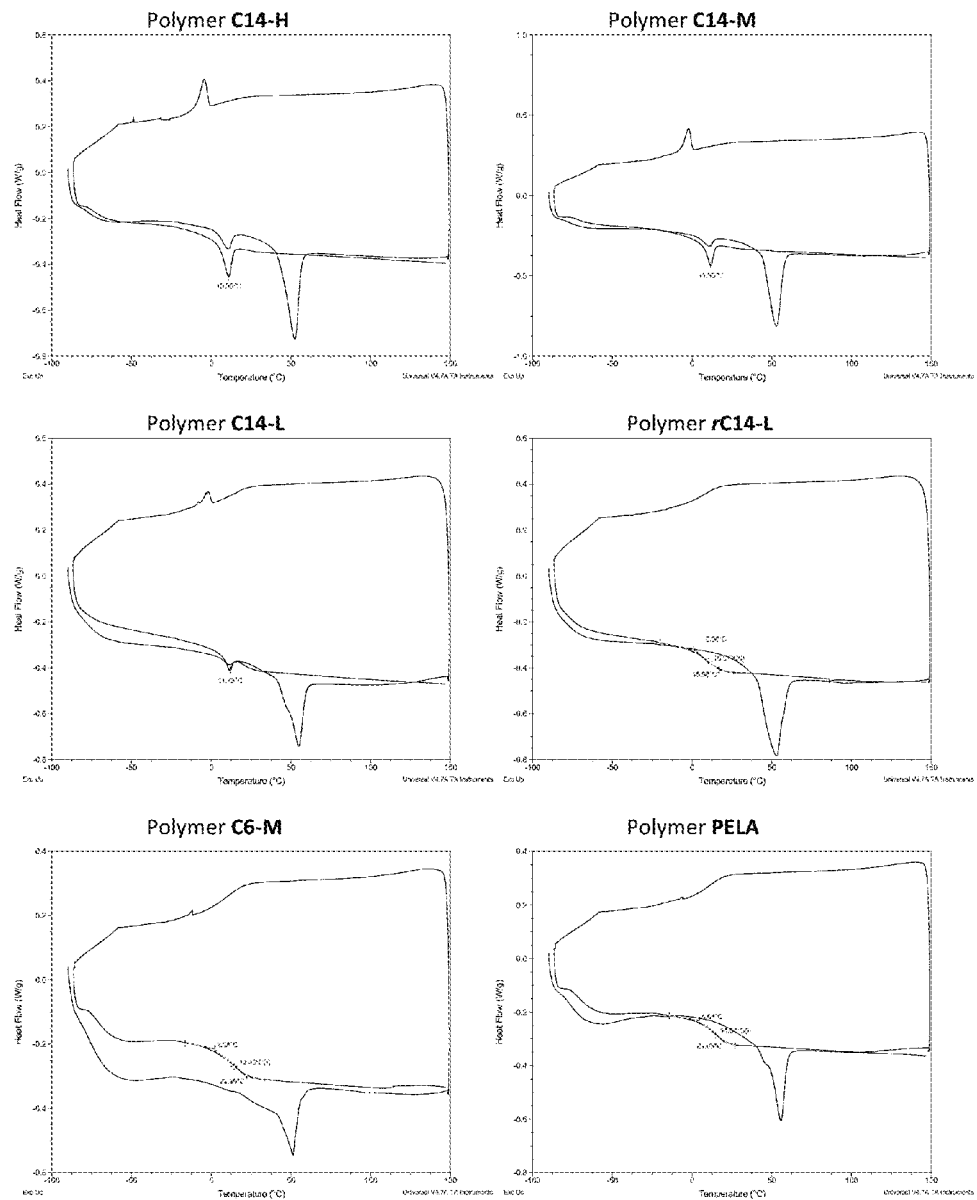
FIG. 9. DSC spectra (first and second heating cycles) of PELA, pentablock and random polymers.

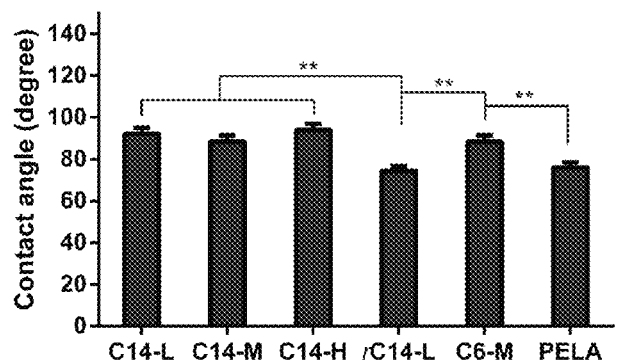
FIG. 10. Water contact angles (n = 10) of dense solvent-cast polymer films. **P<0.01 (Student's *t*-test).
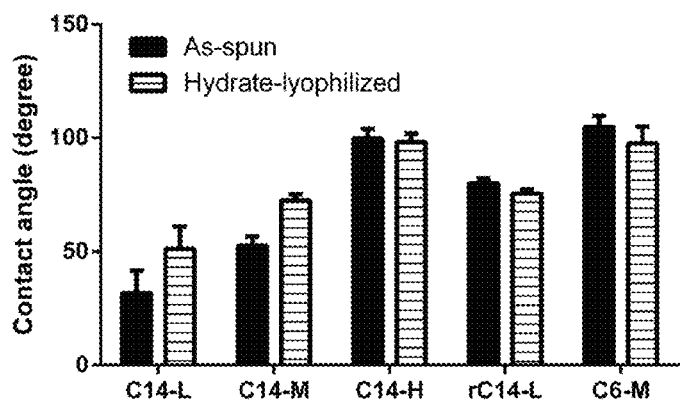
FIG. 11. Water contact angles (n = 7) of as-spun meshes vs. lyophilized meshes following 24-h hydration.

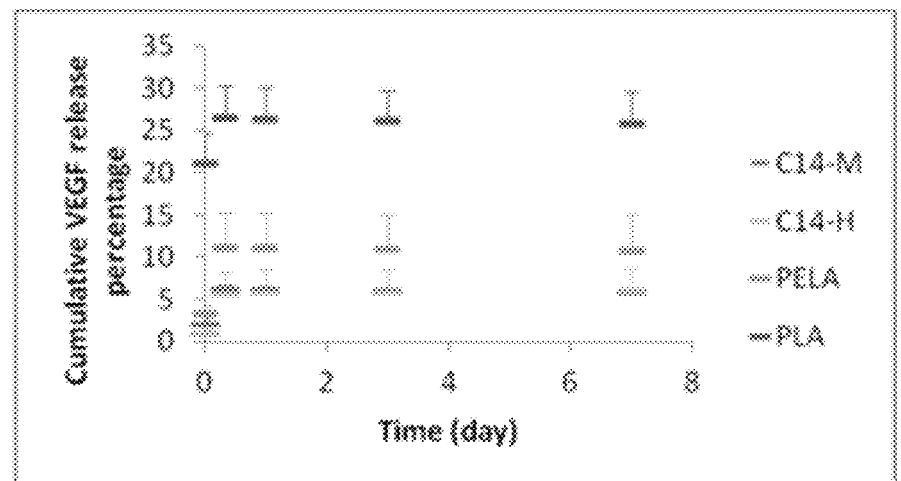
FIG. 12. Loading dose: 10-ng rhVEGF165/mesh
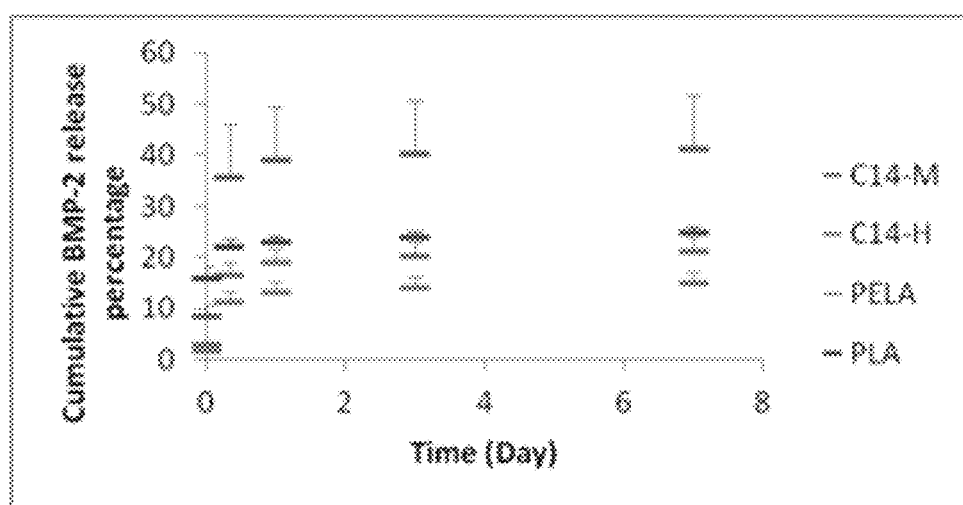
FIG. 13. Loading dose: 10-ng rhBMP-2/mesh

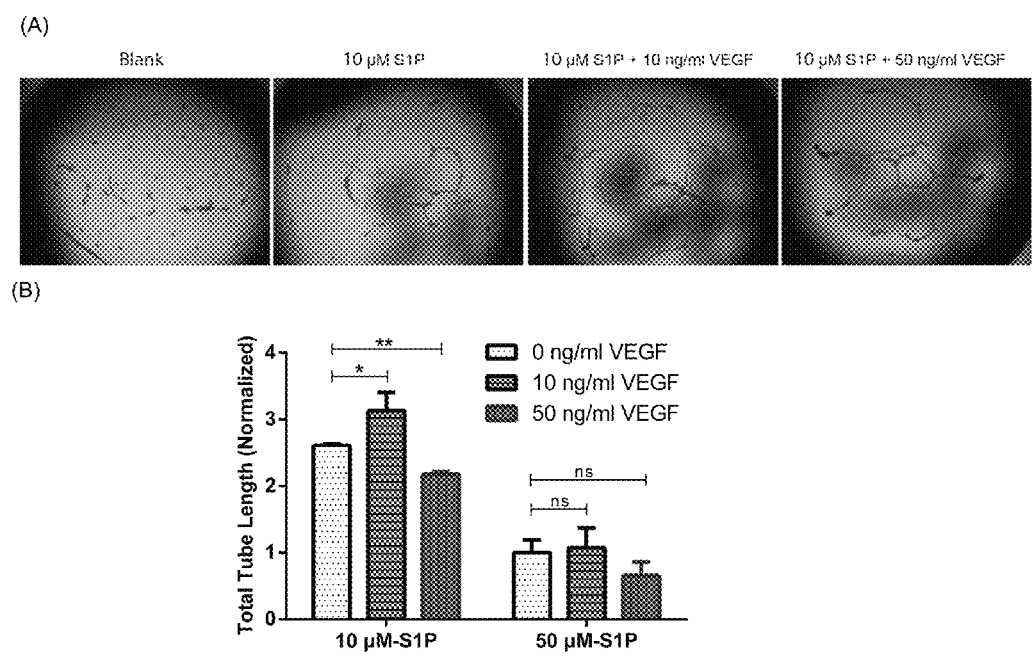
FIG. 14. (A) Representative tube formation of HUVECs cultured with or without the supplements of S1P alone, and S1P in combination of a lower or higher dose of VEGF. (B) The total tube length in each well (n = 3) as quantified by ImageJ (NIH). Data are plotted as mean ± standard derivation. $*P < 0.05$, $**P < 0.01$ (student t-test).

AMPHIPHILIC DEGRADABLE POLYMERS FOR IMMOBILIZATION AND SUSTAINED DELIVERY OF BIOMOLECULES

PRIORITY CLAIMS AND CROSS REFERENCE TO RELATED APPLICATIONS

This application is the U.S. national phase of and claims priority to PCT/US15/17640, filed Feb. 26, 2015, which claims the benefit of priority from U.S. Provisional Application Ser. No. 61/945,117, filed Feb. 26, 2014, the entire content of each of which is incorporated herein by reference in its entirety.

STATEMENT REGARDING FEDERALLY FUNDED RESEARCH

This invention was made with government support under Grant No. AR055615 awarded by the National Institutes of Health. The Government has certain rights in the invention.

TECHNICAL FIELD OF THE INVENTION

The invention generally relates to controlled delivery of biomolecules. More particularly, the invention relates to amphiphilic degradable polymers, their preparation, and related methods for immobilization and controlled delivery of biomolecules (e.g., lipids, proteins) thereof.

BACKGROUND OF THE INVENTION

The delivery of biomolecules, including lipids and therapeutic proteins, provides a promising vehicle for the treatment of many diseases and conditions, such as angiogenesis. Angiogenesis is essential for tissue development, function, maintenance, repair and regeneration. Impaired angiogenesis due to either injuries or diseases can severely impair these processes. (Carano et al. 2003 *Drug Discov Today* 8:980-9; Laschke et al. 2006 *Tissue Eng* 12:2093-104; Harris et al. 2013 *Curr Pharm Des* 19:3456-65; Novosel et al. 2011 *Adv Drug Deliv Rev* 63:300-11; Nguyen et al. 2012 *Tissue Eng Part B Rev* 18:363-82.) For instance, disruption of vascular network as a result of orthopedic trauma compromises the ability to vascularize bone grafts, resulting in high clinical failure rates of bone graft-mediated repair of traumatic bone defects. (Ito et al. 2005 *Nat Med* 11:291-7.) In pathological conditions such as diabetes, the microangiopathic complication/tissue ischemia also retards bone injury repair and graft healing as it disrupts the tightly coupled osteogenesis and angiogenesis processes. (Abaci et al. 1999 *Circulation* 99:2239-42; Waltenberger et al. 2001 *Cardiovasc Res* 49:554-60; Kanczler et al. 2008 *Eur Cell Mater* 15:100-14.)

Therapeutic strategies for promoting angiogenesis, particularly the formation of functional and stable vascular network, have long been sought after in scaffold-assisted tissue repair and regeneration. Angiogenesis involves a dynamic cascade of cellular and molecular events involving early-stage of lumen formation (e.g., increased blood vessel permeability, basement membrane degradation, endothelial cell (EC) migration, proliferation and further assembly into tubular structure) and later-stage of nascent EC tube stabilization and maturation (e.g., mural cells recruitment and new basement membrane deposition). (Carmeliet et al. 2011 *Nature* 473:298-307; Potente et al. 2011 *Cell* 146:873-87.) The entire angiogenesis process is tightly regulated by a dynamic balance of pro-angiogenic factors and vessel-stabilizing factors. (Jain 2003 *Nat Med* 9:685-93.)

Current strategies for recapitulating this process in-situ involve the delivery of angiogenic stimuli, of which angiogenic growth factor such as vascular endothelial growth factor (VEGF) is the most intensively studied. (Nguyen et al. 2012 *Tissue Eng Part B Rev* 18:363-82; Baiguera et al. 2013 *Angiogenesis* 16:1-14; Cenni et al. 2011 *Acta Pharmacol Sin* 32:21-30; Said et al. 2013 *J Vasc Res* 50:35-51; Mehta et al. 2012 *Adv Drug Deliv Rev* 64:1257-76; Tayalia et al. 2009 *Adv Mater* 21:3269-85.) VEGF is a potent angiogenesis initiator that is also known to disrupt pericyte coverage and inhibit subsequent vessel stabilization, thus the delivery of exogenous VEGF alone often results in sub-optimal neo-vascularization characterized with immature "leaky" vessels. (Greenberg et al. 2008 *Nature* 456:809-13.)

Therefore, the delivery of alternative/complementary signaling molecules promoting the formation of more extensive, stable and functional vascular network are highly desired. Phospholipid sphingosine 1-phosphate (S1P) has emerged as such a promising candidate because of its dual role as angiogenic stimulant and blood vessel stabilizer.

During the early stages of angiogenesis, S1P acts as a potent EC chemoattractant, promoting EC proliferation, migration and further assembly into tubes while S1P receptor 1 (S1P1) negatively regulates vessel sprouting to prevent excessive sprouting. (English et al. 2000 *FASEB J* 14:2255-65; Yatomi et al. 2000 *Blood* 96:3431-8; Kimura et al. 2000 *Biochem J* 348 Pt 1:71-6; Lee et al. 1999 *Cell* 99:301-12; Shoham et al. 2012 *Development* 139:3859-69; Gaengel et al. 2012 *Dev Cell* 23:587-99.) In the later stages of angiogenesis, S1P regulates vasculature remodeling and maturation by recruiting vascular smooth muscle cells (VSMC) and pericytes. (Takuwa et al. 2010 *World J Biol Chem* 1:298-306; Paik et al. 2004 *Genes Dev* 18:2392-403; Liu et al. 2000 *J Clin Invest* 106:951-61; Allende et al. 2003 *Blood* 102:3665-7.)

Studies support potential benefits of the delivery of S1P in improving the functional outcome of tissue repair. The local delivery of S1P or S1P analogue FTY 720 has been shown to enhance wound healing in diabetic rats, stimulate blood flow in ischemic limbs, and promote calvarial bone formation and allograft incorporation. (Kawanabe et al. 2007 *J Dermatol Sci* 48:53-60; Qi et al. 2010 *Eur J Pharmacol* 634:121-31; Sefcik et al. 2008 *Biomaterials* 29:2869-77; Petrie et al. 2010 *Tissue Eng Part A* 16:1801-9; Das et al. 2013 *J Biomed Mater Res A*: doi/10.1002/jbm.a.34779; Petrie et al. 2010 *Biomaterials* 31:6417-24; Huang et al. 2012 *Cell Tissue Res* 347:553-66.)

There are few existing biomaterials that can adequately meet the requirements of the tunable and sustained delivery of such amphiphilic molecules. Poly(lactic-co-glycolic acid) (PLGA) is commonly used for S1P delivery by physical blending or microsphere fabrication (Qi et al. 2010 *Eur J Pharmacol* 634:121-31; Sefcik et al. 2008 *Biomaterials* 29:2869-77; Petrie et al. 2010 *Tissue Eng Part A* 16, 1801-9). The release of S1P in these materials is mainly dominated by passive S1P diffusion and polymer scaffold hydrolytic degradation, which are poorly controlled by nature. The other material attempted for S1P delivery is polyethylene glycol (PEG)-based hydrogels cross-linked by albumin (Wacker et al. 2006 *Biomacromolecules* 7, 1335-43). The disadvantages of the system include multi-step chemical synthesis, complicated hydrogel formulation and the requirement of preloading of drug cargo in order to achieve reasonable eluting profiles. The hydrogel itself per se does not possess intrinsic structural tunability to enable manipulation of the S1P release kinetics.

Recently a cellulose hollow fiber-based system enabling timed delivery of S1P following earlier release of VEGF was shown to result in greater recruitment of ECs and higher maturation index of formed vessels in a Matrigel plug model. (Tengood et al. 2010 *Biomaterials* 31:7805-12.) However, this delivery system required external manual regulation, which complicates its implementation for in vivo tissue regeneration. Overall, synthetic scaffolds demonstrating significantly improved S1P loading efficiency and more tunable S1P release kinetics is still lacking.

Thus, a significant challenge for translating the S1P-based proangiogenic strategy to successful tissue repair is the lack of a tunable sustained release system enabling the optimization of its release kinetics for maximal stimulation of vessel formation and maturation. It is strongly desired that novel approaches and techniques be developed that enable controlled immobilization and delivery of biomolecules such as lipids and proteins.

SUMMARY OF THE INVENTION

The invention provides a novel approach to controlled delivery of biomolecules (e.g., lipids and proteins) by employing novel amphiphilic degradable polymers as delivery vehicles. These unique polymers may be utilized as tissue engineering scaffolds wherein the delivery of lipophilic or amphiphilic bioactive molecules can be effectively achieved.

An amphiphilic biodegradable polymer platform is disclosed herein for the stable encapsulation and sustained release of biomolecules, such as S1P. Mimicking the interaction between amphiphilic S1P and its binding proteins, a series of polymers with hydrophilic poly(ethylene glycol) core and lipophilic flanking segments of polylactide and/or poly(alkylated lactide) with different alkyl chain lengths were synthesized. These polymers were electrospun into fibrous meshes, and loaded with S1P in generally high loading efficiencies (>90%). Sustained S1P release from these scaffolds can be tuned by adjusting the alkyl chain length, blockiness and lipophilic block length, achieving 35-55% and 45-80% accumulative releases in the first 8 h and by 7 days, respectively. Furthermore, using endothelial cell tube formation assay and chicken chorioallantoic membrane (CAM) assay, it was shown that the different S1P loading doses and release kinetics translated into distinct pro-angiogenic outcomes.

In one aspect, the invention generally relates to an amphiphilic degradable block copolymer, which includes hydrophilic blocks; flanking lipophilic blocks; and lipophilic blocks having pendent alkyl chains of lengths from about $C_6$ to about $C_{24}$;

In another aspect, the invention generally relates to an amphiphilic degradable random copolymer, which includes hydrophilic monomer units, having the structure of

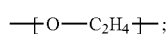

lipophilic monomer units, having the structure of

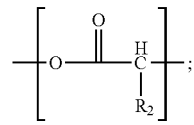

and lipophilic monomer units, having the structure of

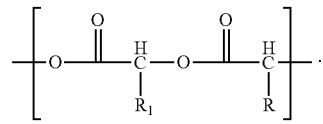

wherein
each of $R_1$ and $R_2$ is hydrogen or a $C_1$-$C_2$ alkyl group;
R is a linear or substantially linear alkyl chain of a length from about $C_6$ to about $C_{24}$.

In certain preferred embodiments, the amphiphilic degradable random copolymer, each of $R_1$ and $R_2$ is a methyl group; and R is a linear alkyl chain of a length from about $C_6$ to about $C_{18}$.

In another aspect, the invention generally relates to a fibrous scaffold made from an amphiphilic degradable copolymer of the invention.

In yet another aspect, the invention generally relates to a method for sustained release of a biomolecule to an in vivo target location. The method includes: providing a fibrous scaffold prepared from an amphiphilic degradable copolymer of the invention; loading the fibrous scaffold with the biomolecule to be delivered in vivo; placing the loaded fibrous scaffold at the target location; and causing sustain release of the biomolecule at the target location.

Figure 1:
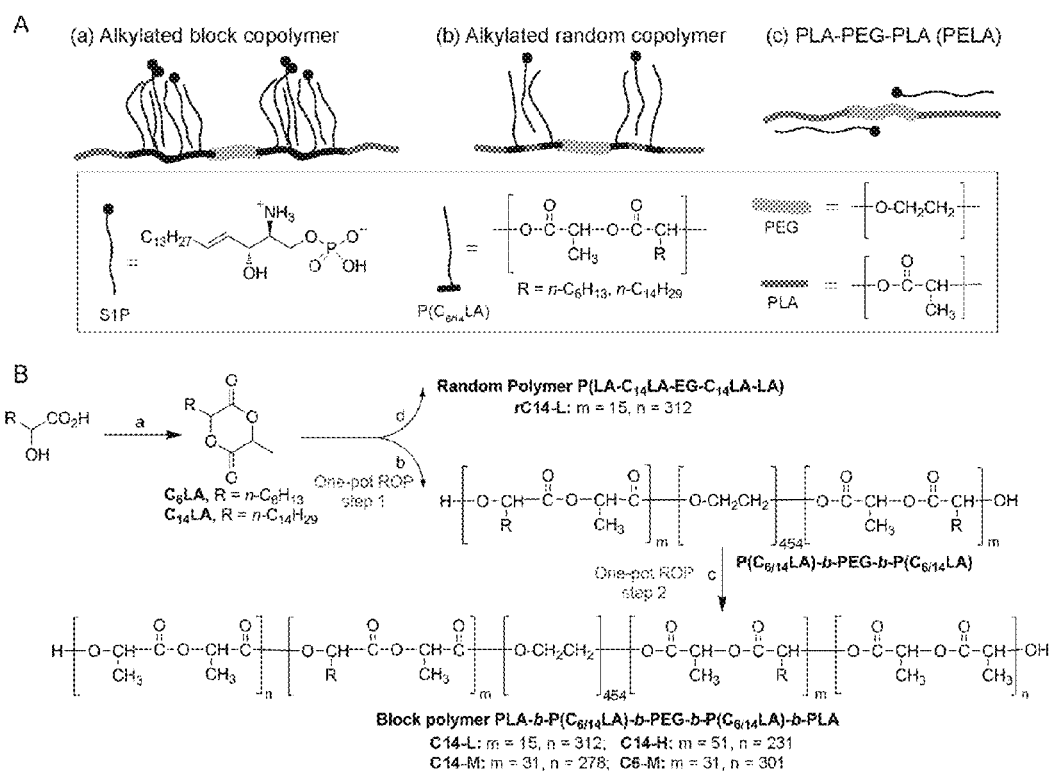
FIG. 1. (A) Schematic illustration of possible interactions between S1P and the amphiphilic polymers. (B) Synthetic schemes for the alkylated lactides and amphiphilic polymers. Reagents and conditions: (a) 2-bromopropionyl bromide (1.05 eq.), Et3N (2.0 eq.), acetone, rt for 0.5 h, then filtered; Et3N (2.0 eq.), 65° C. for 2 h. (b) PEG20K, Sn(Oct)2, 150° C., 30 min. (c) D,L-lactide, 150° C., 60 min. (d) PEG20K, D,L-lactide, Sn(Oct)2, 150° C., 60 min.

(A) Representative photographs of the CAM surrounding the meshes with/without S1P (16×mag.) at day 0 and day 3, and the photographs of the flipped side of the harvested CAM on day 3 (25×mag.) of the boxed area. (B) Quantification of microvessel numbers surrounding each scaffold (n=4).

FIG. 8. DSC spectra (second heating cycle) of PEG20K vs. the C14- and C6-alkylated triblock copolymers.

FIG. 9. DSC spectra (first and second heating cycles) of PELA, pentablock and random polymers.

FIG. 10. Water contact angles (n=10) of dense solvent-cast polymer films. **P<0.01 (Student's t-test).

FIG. 11. Water contact angles (n=7) of as-spun meshes vs. lyophilized meshes following 24-h hydration.

FIG. 12. Protein delivery: Loading dose of 10-ng rhVEGF165/mesh.

FIG. 13. Protein delivery: Loading dose of 10-ng rhBMP-2/mesh.

FIG. 14. (A) Representative tube formation of HUVECs cultured with or without the supplements of S1P alone, and S1P in combination of a lower or higher dose of VEGF. (B) The total tube length in each well (n=3) as quantified by ImageJ (NIH). Data are plotted as mean±standard derivation. *P<0.05, **P<0.01 (student t-test).

DETAILED DESCRIPTION OF THE INVENTION

The invention provides a novel approach for controlled delivery of biomolecules. Amphiphilic degradable polymers disclosed herein can be employed to effectively immobilize and deliver biomolecules such as lipids and proteins. For example, emulating the amphiphilic interactions of angiogenic lipid S1P with its natural binding proteins, the electrospun amphiphilic degradable copolymer platform of the invention allows for highly efficient S1P loading and sustained release. It is demonstrated that S1P release profiles can be fine tuned by incorporating alkylated polylactides with side chains of select length to amphiphilic triblock copolymer PLA-PEG-PLA (PELA). Various spatial distributions (block vs. random) and clustering densities (high, medium and low) can be used in fine turning the desired release profile.

Structurally, S1P is an amphiphilic lysophospholipid comprised of a zwitterionic head group and a hydrophobic 18-carbon (C18) aliphatic tail. In circulating blood, S1P is released from platelets in micromolar concentrations and most of the released S1P is stored by binding with albumin and lipoproteins such as high-density lipoprotein (HDL). (Yatomi et al. 2000 *Blood* 96:3431-8; Rivera et al. 2008 *Nat Rev Immunol* 8:753-63; Aoki et al. 2005 *J Biochem* 138:47-55; Murata et al. 2000 *Biochem J* 352:809-15; Sachinidis et al. 1999 *Arterioscler Thromb Vasc Biol* 19:2412-21.) Recent structural studies revealed that the interaction of S1P with HDL is mediated by HDL-associated apolipoprotein M (apoM). Specifically, apoM was shown to have an amphiphilic binding pocket with a polar entrance to grab the hydrophilic S1P headgroup and an inner lipophilic pocket to accommodate the C18 aliphatic tail. (Arkensteijn et al. 2013 *Int J Mol Sci* 14:4419-31; Christoffersen et al. 2011 *Proc Natl Acad Sci USA* 108:9613-8.) This amphiphilic interaction pattern is also observed with the bindings of S1P antagonist with S1P1 receptor and S1P with S1P antibody. (Hanson et al. 2012 *Science* 335:851-5; Wojciak et al. 2009 *Proc Natl Acad Sci USA* 106:17717-22.)

The amphiphilic polymers of the invention represent a unique biomimetic strategy to realize biomolecule immobilization and tunable sustained release through reversible amphiphilic interactions. As disclosed herein, the amphiphilic polymer scaffold incorporating both hydrophobic and hydrophilic segments effectively binds S1P, mimicking the natural amphiphilic interaction pattern, which translates into improved S1P loading efficiency. Furthermore, the release kinetics of the encapsulated S1P can be tuned by adjusting the lipophilicity of the polymer, for example, with a PLA-PEG-PLA (PELA)-based amphiphilic block copolymer platform incorporating alkylated lactides. (Kutikov et al. 2013 *Acta Biomater* 9:8354-64.) By varying alkyl side chain lengths, blockiness and block lengths, one can utilize the impact of these factors on the encapsulation, release and angiogenic outcome of S1P delivery.

The polymers of the invention can be synthesized with conventional ring opening polymerization (ROP) and electrospun into fibrous meshes. Examples of synthesized polymers are three C14-alkylated pentablock copolymers (C14-H, C14-M, C14-L) containing high, medium and low C14-block lengths relative to the hydrophilic PEG core, one C6-alkylated pentablock copolymer (C6-M) containing medium C6 block length, one C14-alkylated random copolymer (rC14-L), and the triblock copolymer PELA without alkyl side chains. These polymers were subjected to detailed comparative studies.

Figure 3:
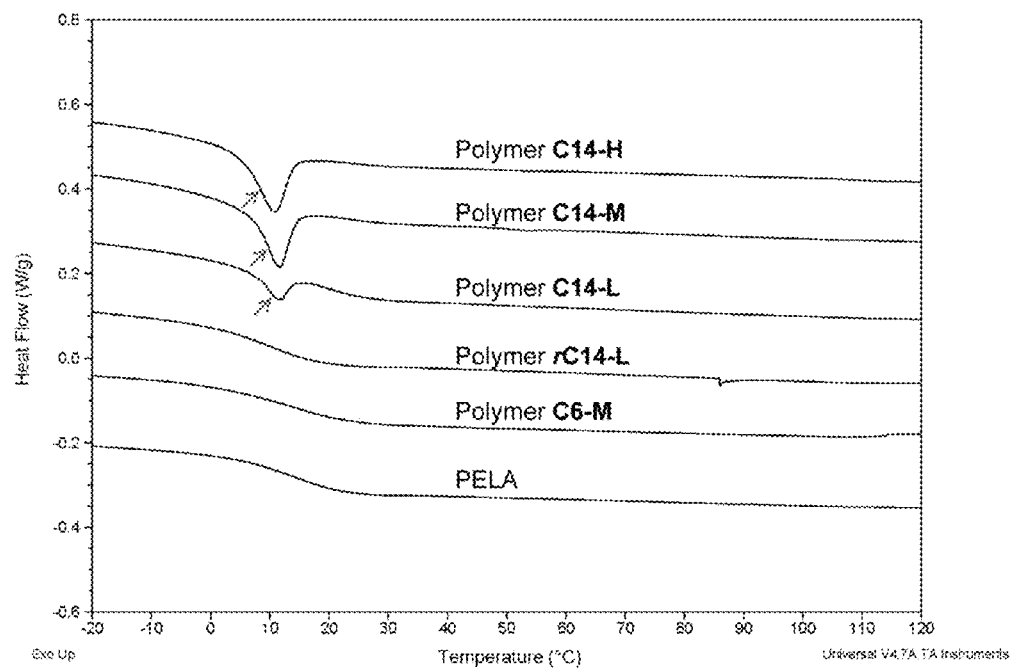
FIG. 3. DSC spectra of PELA, pentablock and random copolymers.

Thermal analysis of the amphiphilic polymers by DSC revealed an endothermic peak at 10-12° C. ascribable to alkyl-alkyl aggregations in C14-block polymers, but not in the C6-block or C14-random copolymers (FIG. 3). These observations suggest that adequate interactions between clustered (blocky) alkyl side chains of critical length is required for creating the hydrophobic "pocket" desired for trapping the lipid tail of S1P. SEM micrographs of the electrospun meshes (FIG. 4A) and the porosities calculated from the weight ratios of the porous meshes to the dense films (FIG. 4B) revealed varying fiber morphologies and porosities.

Figure 4:
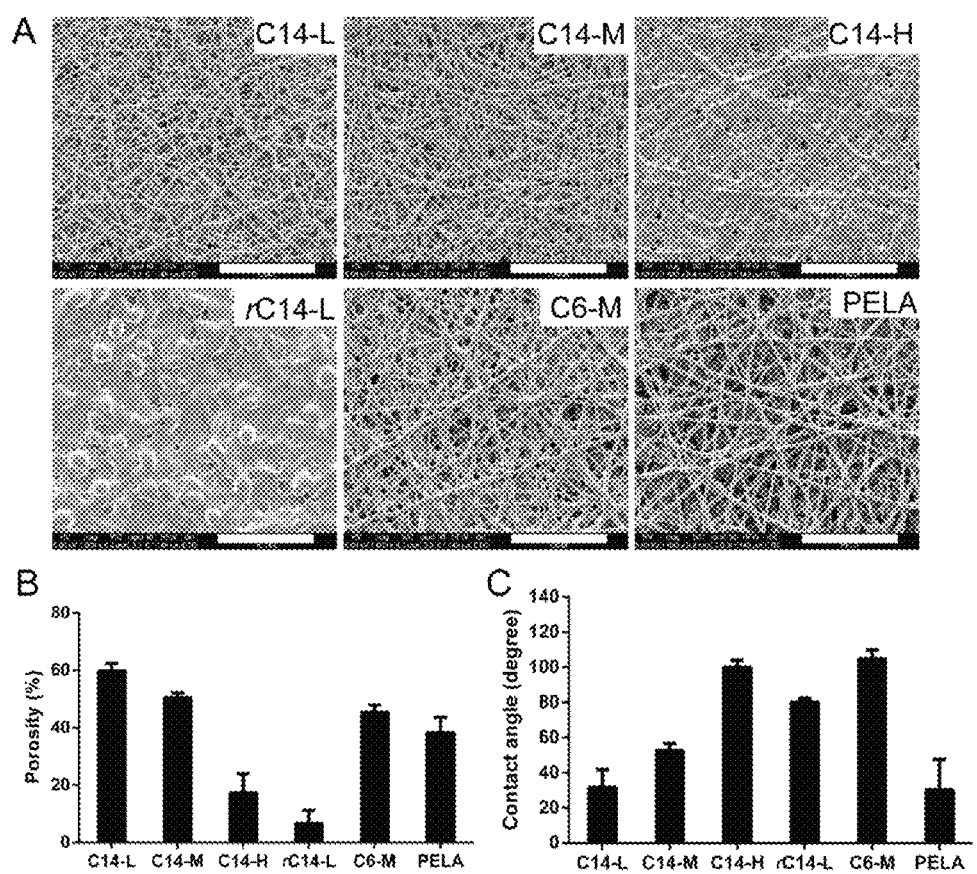
FIG. 4. (A) SEM micrographs, (B) calculated mesh porosity (n=3) and (C) water contact angles (n=7) of electrospun fibrous meshes. Scale bar=50 μm.

While the C6-M, C14-M, C14-L and the unalkylated PELA meshes were characterized with medium (40-60%) porosity and well-defined fibers free of beading, the electrospun C14-H fibers exhibited some degrees of fusing, resulting in lower porosity (<20%). The random polymer rC14-L was unsuited for electrospinning, resulting in low-porosity (<10%) meshes lacing well-defined fiber morphology. The differential porosities, in combination with the intrinsic hydrophilicity of the amphiphilic copolymers as reflected by the water contact angles of the dense solvent-cast films (FIG. 10), translated into significant differences in the wettability of the electrospun meshes (FIG. 4C).

The S1P loading efficiency and release kinetics was governed by both the thermal and physical properties of the alkylated amphiphilic polymer meshes. At room or body temperature, the intramolecular alkyl-alkyl aggregation is expected to undergo a dynamic equilibrium of association and disassociation, allowing S1P to be reversibly sequestered/released from the aggregated hydrophobic "pocket", a characteristic desired for controlled and sustained release of S1P. Indeed, dynamic hydrophobic interactions appeared to have played a prominent role than the mesh porosity in ensuring high S1P loading efficiency with block copolymers with longer alkyl side chains (FIG. 5A, >90% loading efficiency for C14-L, C14-M and C14H vs. ~55-65% for C6-M and rC14-L). The relatively low mesh porosity and wettability of C14-H electrospun mesh did not compromise its ability to support high S1P loading efficiency.

Figure 5:
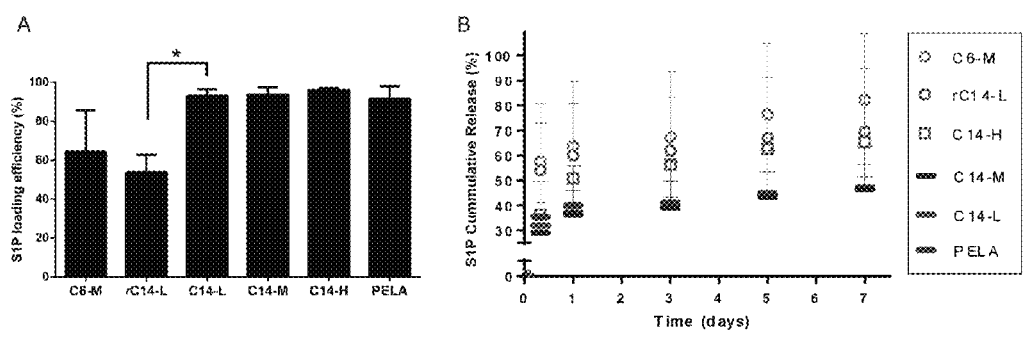
FIG. 5. (A) S1P loading efficiencies (n=3) on polymeric fibrous meshes and (B) their cumulative releases over time (n=3) in PBS with 0.2% FAF-BSA.

The differential hydrophobic interactions between these amphiphilic alkylated polymers and S1P (FIG. 1A) also translated into distinct S1P release profiles (FIG. 5B). The less effective sequestering of S1P by the C6-M and rC14-L resulted in more rapid early release (~55% in the first 8 h) followed by substantial continued release (70-80% cumulative release in 7 days). C14-H displayed the most sustained and steady release of S1P, amounting to 35% in the first 8 h and 65% accumulative release by day 7. C14-M and C14-L exhibited very similar, and the slowest S1P release, totaling 30-35% in the first 8 h but no more than 10% additional S1P release in the next 7 days. The more substantial S1P release from mesh C14-H than those from C14-M or C14-L could in part be a result of its relatively low porosity (FIG. 4B), which may have resulted in S1P encapsulation more towards the surface (thus easier release). It is worth noting that due to the varying S1P loading methods, releasing conditions, detection methods adopted by literature reports, direct quantitative comparison of the S1P loading efficiency and release kinetics with literature carriers is difficult, although the high loading efficiency accomplished with the C14-alkylated system was excellent. (Qi et al. 2010 *Eur J Pharmacol* 634:121-31; Petrie et al. 2010 *Biomaterials* 31:6417-24; Wacker et al. 2006 *Biomacromolecules* 7:1335-43.)

Interestingly, PELA displayed S1P loading and release kinetics similar to those of alkylated polymers C14-L and C14-M, despite its lack of alkylated side chains. One possible explanation may be that the amphiphilic PELA binds S1P through different mode of molecular interactions. Previous studies showed that PELA could undergo a conformation rearrangement upon contact with water, exposing the hydrophilic PEG blocks to the polymer/water interface. (Kutikov et al. 2013 *Acta Biomater* 9:8354-64.) Such a hydration-induced structural rearrangement may strengthen the hydrophobic interaction between its PLA blocks and the lipid tail of the S1P. For the alkylated amphiphilic copolymers, the mobility of the PLA segments may have been hindered due the steric constraints imposed by the aliphatic side chains, thereby minimizing S1P sequestration through this mechanism. This was supported by the differential changes in water contact angles of the amphiphilic meshes upon 24-h hydration (FIG. 11). Unlike PELA, which exposed its hydrophilic PEG segments upon prior hydration to result in significant reduction in water contact angles, the alkylated amphiphilic polymers exhibited similar or slightly higher water contact angles, supporting that their PEG segments did not effectively expose to surface upon hydration. (Kutikov et al. 2013 *Acta Biomater* 9:8354-64.)

The benefit of sustained delivery of S1P via a suitable scaffold was demonstrated in HUVEC-Matrigel tube formation assay and CAM assay. Unlike high doses (e.g., 50 μM) of free S1P solution that could pose inhibitory effect on tube formation, the same dose of S1P, when encapsulated/released by amphiphilic scaffolds, promoted EC tube formations. (Kohno et al. 2008 *Genes Cells* 13:747-57.) Such a benefit was more pronouncedly manifested by the C14-H and C14-M scaffolds than the C6-M mesh, which exhibited most rapid early release of S1P. Using a 3-day ex ovo CAM assay, it was further demonstrated that C14-H mesh, with more sustained S1P release kinetics, led to significantly more neovessel formation and capillary bending/infiltration than the C6-M mesh. Collectively, these observations support that controlled S1P release can be functionally translated into pro-angiogenic activities both in vitro and ex ovo.

The tunable S1P loading efficiency, release profile, and in vitro and ex ovo pro-angiogenic activities enabled by the amphiphilic copolymer platform presented in this study provides a unique opportunity for optimizing angiogenesis for tissue repair/regeneration. A recent study demonstrated superior aqueous stability, tensile elasticity, osteoconductive and osteoinductive properties of the bone mineral composites of amphiphilic copolymer PELA compared to those based on the hydrophobic PLA. (Kutikov et al. 2013 *Acta Biomater* 9:8354-64.) These benefits, likely retained with the amphiphilic copolymer platform presented here, may be combined with the controlled S1P delivery to synergistically promote osteogenesis and angiogenesis, thereby improving the outcome of scaffold-assisted bone repair. However, the in vivo efficacy of such a strategy will need to be rigorous examined using suitable animal models.

The alkylated amphiphilic polymers disclosed in this invention can be used alone, or as a carrier for bioactive lipids such as S1P, proteins and other amphiphilic biomolecules. They can also be used in combination with other polymers, osteoconductive minerals, osteoinductive growth factors, or cells. Depend on specific applications, the polymers or their combination can be formulated into: (1) scaffolds such as bone graft, vascular graft and peripheral nerve graft; (2) biodegradable coatings for drug-eluting stents; (3) microspheres and hydrogels for localized drug delivery; (4) films as wound dressing for skin regeneration, diabetic foot ulcer or guided bone regeneration; (5) sutures, pins, plates, screws and other surgery tools.

Thus, in one aspect, the invention generally relates to an amphiphilic degradable block copolymer, which includes hydrophilic blocks; flanking lipophilic blocks; and lipophilic blocks having pendent alkyl chains of lengths from about $C_6$ to about $C_{24}$;

In certain preferred embodiments of the amphiphilic degradable block copolymer, the hydrophilic blocks comprise blocks of poly(ethylene glycol) having the structure of

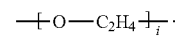

The flanking lipophilic blocks comprise blocks of polylactide having the structure of

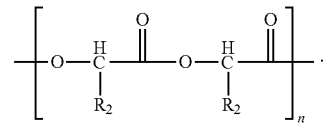

The lipophilic blocks having pendent alkyl chains comprise poly(alkylated lactide) having the structure of

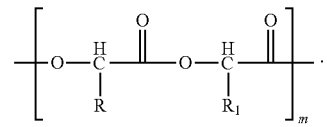

Each of $R_1$ and $R_2$ is independently hydrogen or a $C_1$-$C_2$ alkyl group (e.g., methyl, ethyl). Each R is independently a linear or substantially linear alkyl chain of a length from about $C_6$ to about $C_{24}$ (e.g., a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or $C_{26}$ alkyl chain). i is an integer from about 10 to about 5,000 (e.g., from about 10 to about 4,000, from about 10 to about 3,000, from about 10 to about 2,000, from about 10 to about 1,000, from about 10 to about 500, from about 20 to about 5,000, from about 50 to about 5,000, from about 100 to about 5,000, from about 200 to about 5,000, from about 500 to about 5,000). m is an integer from about 1 to about 1,000 (e.g., from about 1 to about 800, from about 1 to about 500, from about 1 to about 300, from about 1 to about 200, from about 1 to about 100, from about 1 to about 50, from about 10 to about 1,000, from about 50 to about 1,000, from about 100 to about 1,000, from about 200 to about 1,000, from about 500 to about 1,000). n is an integer from about 10 to about 5,000 (e.g., from about 10 to about 4,000, from about 10 to about 3,000, from about 10 to about 2,000, from about 10 to about 1,000, from about 10 to about 500, from about 20 to about 5,000, from about 50 to about 5,000, from about 100 to about 5,000, from about 200 to about 5,000, from about 500 to about 5,000).

In certain preferred embodiments, the amphiphilic degradable block copolymer includes the structure of

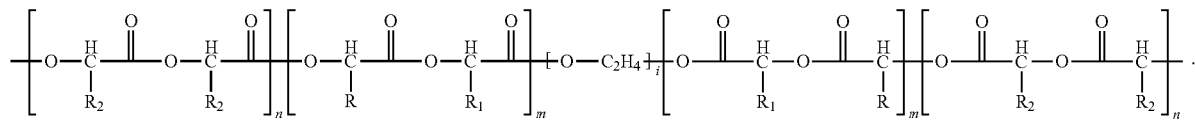

In certain preferred embodiments, each of $R_1$ and $R_2$ is independently a $C_1$-$C_2$ alkyl group; R is a linear alkyl chain of a length from about $C_{12}$ to about $C_{24}$; i is an integer from about 10 to about 5,000; each m is an integer from about 1 to about 1,000; and each n is an integer from about _10_ to about 5,000.

In certain preferred embodiments of the amphiphilic degradable block copolymer, each of $R_1$ and $R_2$ is a methyl group; R is a linear alkyl chain of a length from about $C_6$ to about $C_{18}$; i is an integer from about 200 to about 800 (e.g., from about 200 to about 600, from about 200 to about 500, from about 200 to about 400, from about 300 to about 800, from about 400 to about 800, from about 500 to about 800); each m is an integer from about 10 to about 100 (e.g., from about 10 to about 80, from about 10 to about 60, from about 10 to about 50, from about 10 to about 30, from about 10 to about 20, from about 20 to about 100, from about 40 to about 100, from about 60 to about 100, from about 80 to about 100); and each n is an integer from about 100 to about 500 (e.g., from about 100 to about 400, from about 100 to about 300, from about 100 to about 200, from about 200 to about 500, from about 300 to about 500, from about 400 to about 500).

The ratio of i:m:n may be any suitable ratio, for example, ranging from about 1~50:1~50:1~50 to about 50~1:50~1:50~1 (e.g., from about 1~30:1~30:1~30 to about 30~1:30~1:30~1, from about 1~20:1~20:1~20 to about 20~1:20~1:20~1, from about 1~10:1~10:1~10 to about 10~1:10~1:10~1, from about 1~5:1~5:1~5 to about 5~1:5~1:5~1).

In certain preferred embodiments, the amphiphilic degradable block copolymer has a molecular weight from about 10,000 to about 1,000,000 (e.g., from about 10,000 to about 500,000, from about 10,000 to about 300,000, from about 10,000 to about 200,000, from about 10,000 to about 100,000, from about 50,000 to about 1,000,000, from about 100,000 to about 1,000,000, from about 200,000 to about 1,000,000, from about 300,000 to about 1,000,000).

In certain preferred embodiments, the amphiphilic degradable block copolymer has a polydispersity from about 1.0 to about 2.0 (e.g., from about 1.0 to about 1.8, from about 1.0 to about 1.6, from about 1.0 to about 1.4, from about 1.2 to about 2.0, from about 1.4 to about 2.0, from about 1.6 to about 2.0).

In another aspect, the invention generally relates to an amphiphilic degradable random copolymer, which includes hydrophilic monomer units, having the structure of

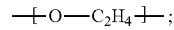

lipophilic monomer units, having the structure of

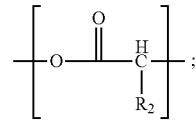

and lipophilic monomer units, having the structure of

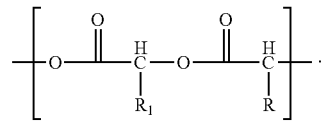

wherein
each of $R_1$ and $R_2$ is hydrogen or a $C_1$-$C_2$ alkyl group;
R is a linear or substantially linear alkyl chain of a length from about $C_6$ to about $C_{24}$.

In certain preferred embodiments, the amphiphilic degradable random copolymer, each of $R_1$ and $R_2$ is a methyl group; and R is a linear alkyl chain of a length from about $C_6$ to about $C_{18}$.

In certain preferred embodiments of the amphiphilic degradable random copolymer, the ratio of hydrophilic units:lipophilic units:lipophilic units with alkyl chains ranges from about 1~50:1~50:1~50 to about 50~1:50~1:50~1. In certain preferred embodiments, the amphiphilic degradable random copolymer has a molecular weight from about 10,000 to about 1,000,000 (e.g., from about 10,000 to about 500,000, from about 10,000 to about 300,000, from about 10,000 to about 200,000, from about 10,000 to about 100,000, from about 50,000 to about 1,000,000, from about 100,000 to about 1,000,000, from about 200,000 to about 1,000,000, from about 300,000 to about 1,000,000).

In certain preferred embodiments, the amphiphilic degradable random copolymer has a polydispersity from about 1.0 to about 2.0 (e.g., from about 1.0 to about 1.8, from about 1.0 to about 1.6, from about 1.0 to about 1.4, from about 1.2 to about 2.0, from about 1.4 to about 2.0, from about 1.6 to about 2.0).

In another aspect, the invention generally relates to a fibrous scaffold made from an amphiphilic degradable copolymer of the invention.

The fibrous scaffold may be loaded with a biomolecule, for example, a lipid or a protein. In certain preferred embodiments, the fibrous scaffold is loaded with S1P at a loading efficiency greater than about 70% (e.g., greater than about 80%, greater than about 90%, greater than about 95%). In certain preferred embodiments, the fibrous scaffold is loaded with rhVEGF at a loading efficiency greater than about 70% (e.g., greater than about 80%, greater than about 90%, greater than about 95%). In certain preferred embodiments, the fibrous scaffold is loaded with rhBMP at a loading efficiency greater than about 70% (e.g., greater than about 80%, greater than about 90%, greater than about 95%).

The fibrous scaffold may take any suitable physical form, for example in the form of selected from fibrous meshes (e.g., by electrospinning), dense films (e.g., by solvent casting), porous 3-D scaffolds (e.g., by salting leaching, gas foaming), dense 3-D scaffolds (e.g., by pressing or extrusion), and macroporous 3-D scaffolds (e.g., fabricated by 3-D prototyping/3-D printing).

In yet another aspect, the invention generally relates to a method for sustained release of a biomolecule to an in vivo target location. The method includes: providing a fibrous scaffold prepared from an amphiphilic degradable copolymer of the invention; loading the fibrous scaffold with the biomolecule to be delivered in vivo; placing the loaded fibrous scaffold at the target location; and causing sustain release of the biomolecule at the target location.

Any suitable biomolecules (e.g., lipids or proteins) may be delivered according to the method of the invention. The biomolecule may be a lipid selected from S1P, ceramide, sphingosine, omega-3 fatty acids such as EPA and DHA. The biomolecule may be a protein selected from VEGF, BMP, FGF, EGF, PDGF and IGF. Any suitable target locations may be selected, for example, bone defect, dental bone defect, craniofacial defect, soft tissue defects such as cartilage and skin defect, composite tissue defects such as osteochondral defect, and any wound surfaces. The sustained releases of the biomolecule ranges from about 8 h to more than 60 days (e.g., from about 8 h to about 60 days, from about 8 h to about 45 days, from about 8 h to about 30 days, from about 8 h to about 14 days, from about 8 h to about 7 days, from about 8 h to about 3 days, from about 12 h to about 60 days, from about 1 day to about 60 days, from about 3 to about 60 days, from about 7 to about 60 days, from about 14 to about 60 days, from about 30 to about 60 days).

Examples

In general, experiments showed that alkylated random copolymers were found to exhibit inferior electrospinability and S1P loading efficiency (~50% vs. >90%) compared with the block copolymers. Furthermore, C6-alkylated block copolymers were found to lead to more rapid early release of S1P (55% in 8 h and 80% in 7 days) comparing with C14-alkylated block copolymers. More sustained and steady release of S1P (35% in 8 h and 65% in 7 days) was accomplished with the C14-block copolymer with long alkylated block length. Much slower release (30-35% in 8 h and 45% in 7 days) was observed with C14-alklyated block copolymer with medium alkylated block length and the unmodified PELA. The interactions between the alkylated amphiphilic copolymers and the S1P appeared to be primarily governed by the tendency of the alkylated side chains and the S1P lipid tail to aggregate (with longer alkyl chains and higher clustering density being more effective in sequestering S1P). By contrast, in the absence of the alkylated side chains, enhanced aggregation of the hydrophobic PLA blocks of PELA upon hydration may be a more dominant factor for the hydrophobic encapsulation of S1P. These distinctive S1P release profiles also translated into varying pro-angiogenic effects in vitro (HUVEC tube formation assay) and ex ovo (CAM assay) in a S1P dose-dependent manner. The benefit of more sustained release of S1P was clearly demonstrated with relatively high S1P encapsulation dose where high concentration of S1P resulting from their burst release could result in inhibitory rather than stimulatory effect on EC tube formations. CAM assay over three days confirmed the proangiogenic and chemotactic effect of S1P-bearing amphiphilic scaffolds. The C14-block copolymer mesh with longer alkylated block length, when encapsulated with S1P and placed on CAM, most effectively induced local neovessel formation and infiltration. Overall, this amphiphilic degradable copolymer platform represents a promising tool for mechanistic investigations of dose and temporal effects of S1P delivery on angiogenesis outcome. Furthermore, it can be exploited for controlled delivery of S1P and other hydrophobic or amphiphilic biomolecules for a wide range of guided tissue regeneration applications.

Synthesis and Characterization of Alkylated Monomers and Amphiphilic Copolymers

Figure 2:
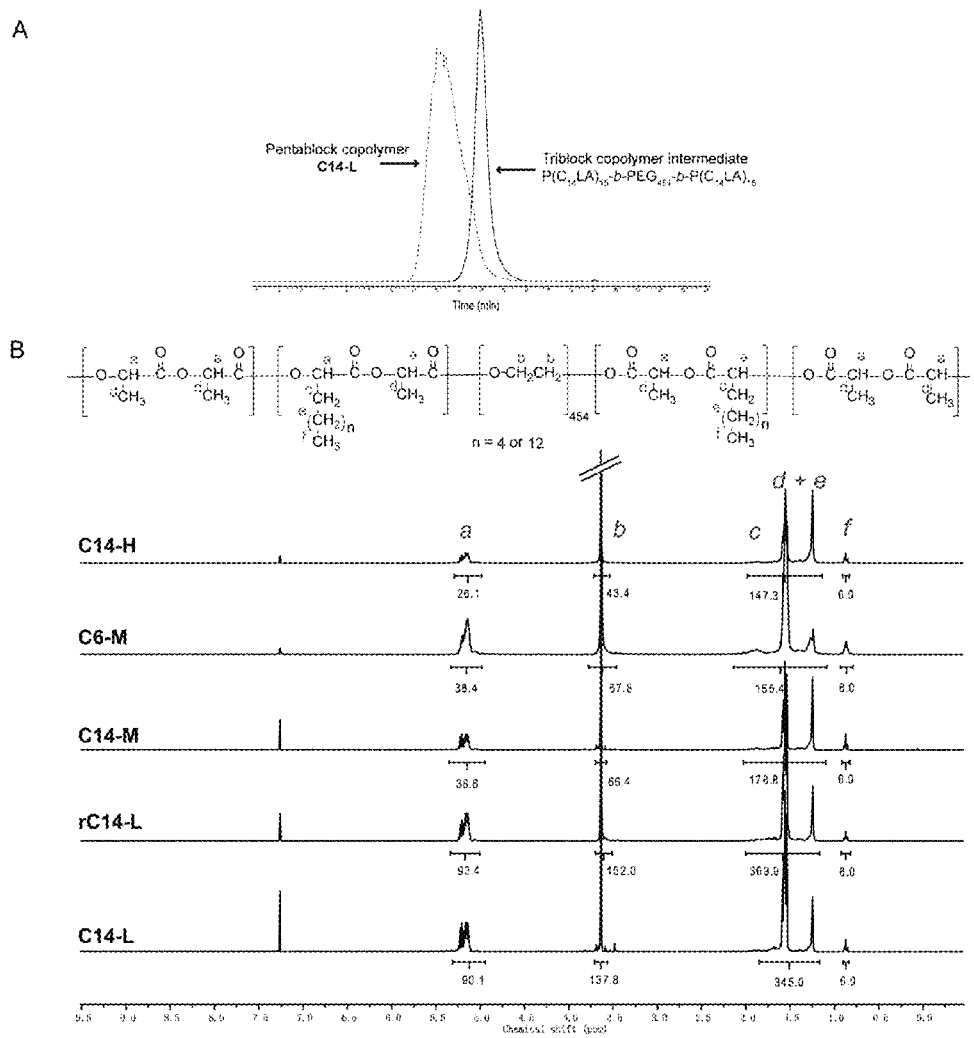
FIG. 2. (A) GPC chromatograms of triblock copolymer intermediate P(C14LA)15-b-PEG454-b-P(C14LA)15 (Mn=34,653, PDI=1.13) and crude pentablock copolymer PLA312-b-P(C14LA)15-b-PEG454-b-P(C14LA)15-b-PLA312 (C14-L, Mn=113,463, PDI=1.47). (B) 1H NMR spectra of the pentablock and random copolymers.

The mono-alkylated lactides $C_6LA$ and $C_{14}LA$ were prepared using a two-step process (FIG. 1B) with an overall moderate yield (largely limited by the intramolecular condensation step) that is consistent with literature. With a targeted molecular weight of 120 kD for all pentablock and random copolymers, melt ROP using PEG20K as a macromolecular initiator and $Sn(Oct)_2$ as catalyst (FIG. 1B) was carried out by simultaneous (for random polymer) or sequential (for block copolymers) addition of alkylated lactides and D,L-lactide (FIG. 1B). PELA of the same targeted molecular weight was also prepared. All polymers were obtained in good yields with high monomer conversions (>90%) and reasonable molecular weight distributions, with PDI of 1.1-1.2 for most triblock copolymers (Table 2) and 1.4-1.5 for pentablock copolymers (Table 1). Decreased number-average molecular weights were observed for triblock copolymers containing increasing theoretical lengths of C14-alkylated blocks (Table 2). GPC comparison of a typical triblock intermediate and final crude pentablock product supported the narrow molecular distributions and high conversions (FIG. 2A). $^1$H NMR integration also supported an overall excellent (80-100%) incorporation of alkylated monomers (FIG. 2B and Table 1). It appeared to be more challenging to obtain high molecular weight random copolymers than the block copolymers (e.g., $M_n^{GPC}$ of rC14-L was 1.5-fold lower than that of the C14-L of same targeted molecular weights).

TABLE 1

Properties of amphiphilic pentablock and random copolymers

| Abbreviation | Polymer Composition[a] | $C_{6/14}LA$:EG (mol:mol) Feeding | $C_{6/14}LA$:EG (mol:mol) Incorporated[b] | Yield (%) | $M_n^{GPC}$ | PDI |
|---|---|---|---|---|---|---|
| Pentablock copolymers | | | | | | |
| C14-L | $LA_{312}$-$(C_{14}LA)_{15}$-$EG_{454}$-$(C_{14}LA)_{15}$-$LA_{312}$ | 1:15.1 | 1:17.2 | 91.7 | 107,282 | 1.47 |
| C14-M | $LA_{278}$-$(C_{14}LA)_{31}$-$EG_{454}$-$(C_{14}LA)_{31}$-$LA_{278}$ | 1:7.3 | 1:8.3 | 86.9 | 79,687 | 1.51 |

TABLE 1-continued

Properties of amphiphilic pentablock and random copolymers

| Abbreviation | Polymer Composition[a] | $C_{6/14}$LA:EG (mol:mol) Feeding | Incorporated[b] | Yield (%) | $M_n^{GPC}$ | PDI |
|---|---|---|---|---|---|---|
| C14-H | $LA_{231}$-$(C_{14}LA)_{51}$-$EG_{454}$-$(C_{14}LA)_{51}$-$LA_{231}$ | 1:4.4 | 1:5.4 | 90.2 | 66,963 | 1.55 |
| C6-M | $LA_{301}$-$(C_{6}LA)_{31}$-$EG_{454}$-$(C_{6}LA)_{31}$-$LA_{301}$ | 1:7.3 | 1:7.2 | 88.9 | 81,059 | 1.48 |
| | Random copolymer | | | | | |
| rC14-L | $LA_{312}$-$(C_{14}LA)_{15}$-$EG_{454}$-$(C_{14}LA)_{15}$-$LA_{312}$ | 1:15.1 | 1:19.0 | 88.0 | 69,251 | 1.49 |

[a]Subscripts refer to the number of repeating units for the respective blocks.
[b]Based on $^1$H NMR integration ratio of the ($CH_2CH_2O$) signal from the PEG to the terminal $CH_3$ signal from the $C_{14}$ or $C_6$ aliphatic side chains.

TABLE 2

Properties of amphiphilic triblock copolymers

| Composition[a] | $M_n^{theo}$ | $M_n^{GPC}$ | PDI | Yield (%) | Physical form |
|---|---|---|---|---|---|
| $(C_6LA)_{25}$-$EG_{454}$-$(C_6LA)_{25}$ | 30,700 | 32,670 | 1.19 | 86.9 | solid |
| $(C_6LA)_{75}$-$EG_{454}$-$(C_6LA)_{75}$ | 52,133 | 46,460 | 1.13 | 51.2 | gel |
| $(C_{14}LA)_{15}$-$EG_{454}$-$(C_{14}LA)_{15}$ | 29,800 | 34,903 | 1.17 | 82.0 | solid |
| $(C_{14}LA)_{25}$-$EG_{454}$-$(C_{14}LA)_{25}$ | 36,300 | 38,144 | 1.15 | 67.3 | solid |
| $(C_{14}LA)_{50}$-$EG_{454}$-$(C_{14}LA)_{50}$ | 52,600 | 36,818 | 1.28 | 72.2 | semi-solid/viscous liquid |
| $(C_{14}LA)_{75}$-$EG_{454}$-$(C_{14}LA)_{75}$ | 69,020 | 39,631 | 1.43 | 83.2 | liquid |
| $LA_{347}$-$EG_{454}$-$LA_{347}$ (PELA) | 120,000 | 87,468 | 1.44 | 91.2 | solid |

[a]Subscript refers to the number of repeating units for each block.

The thermal properties of polymers were examined by DSC to reveal hydrophobic chain-chain interactions, characterized by a thermal transition associated with the aggregation and disassociation of the alkylated side chains. As shown in FIG. 3 and FIG. 9, an endothermic peak at 10.86° C., 11.63° C. and 11.75° C. was detected for C14-alkylated pentablock copolymer C14-H, C14-M and C14-L, respectively, supporting the hydrophobic chain-chain interactions within these amphiphilic pentablock copolymers. However, no such thermal transition was detected in PELA, short chain polymer C6-M or random polymer rC14-L. This thermal transition was also observed in the C14-triblock polymers, but not in the C6-triblock copolymer or PELA (FIG. 8), besides the major endothermic peak at 55-65° C. attributable to PEG crystallization/melting. (Kutikov et al. 2013 Acta Biomater 9:8354-64.)

Polymer Fibrous Mesh Fabrication and Characterization

The amphiphilic polymers were electrospun into fibrous meshes. As shown in FIG. 4A, PELA, C6-M, C14-L and C14-M meshes were composed of randomly arranged microfibers free of beading, with an average fiber diameter of 1.76±0.25 μm, 2.03±0.60 μm, 1.18±0.46 μm and 1.66±0.37 μm, respectively. High-content alkyl side chain incorporation as in the case of C14-H resulted in partial fusion of the fibers, likely driven by hydrophobic interactions between the alkylated segments of contacting fibers at the ambient temperature. The random copolymer rC14-L mesh did not exhibit distinctive fiber morphology, but rather appeared to be composed of fused beading structures, suggesting that this copolymer did not possess optimal physical characteristics (e.g., viscosity) for electrospinning. The quantification of porosity of the electrospun meshes relative to the respective dense solvent-cast films by weight (FIG. 4B) revealed the highest porosity (~60%) for the C14-L mesh, 40-50% porosity for the C14-M, C6-M and PELA meshes, whereas <20% and <10% porosity for C14-H and rC14-L, consistent with the morphologies revealed by SEM micrographs (FIG. 4A).

To examine how the varying surface morphology/porosity and intrinsic hydrophilicity of the polymers translate into differential water wettability, the water contact angles of both electrospun meshes and the respective dense solvent-cast films were measured. Among all dense solvent-cast films (FIG. 10), PELA and rC14-L exhibited significantly lower water contact angle than others, suggesting relatively higher hydrophilicity for PELA and rC14-L. The difference in water contact angles among the dense C14-L, C14-M and C14-H solvent-cast film, however, was not dramatic. The electrospun C14-L, C14-M and C14-H meshes, on the other hand, exhibited significant increases in water contact angles (FIG. 4C), accompanying the decreasing porosity of these electrospun fiber meshes (FIG. 4B), as the content of C14-alkyl side chains increased, supporting significant contributions of surface porosity to the water wettability of the meshes. Overall, C14-L and PELA meshes were the most wettable by water (contact angles ~30°), while the C14-H and C6-M meshes were the least wettable among all (water contact angle ~100°). The least porous (<10%) yet one of the most hydrophilic (FIG. 10) rC14-L electrospun mesh exhibited a water contact angle (~80°) between that of C14-H and C14-M meshes, supporting that surface porosity and polymer hydrophilicity synergistically contribute the overall wettability of the fibrous mesh.

In-Vitro S1P Loading and Release

The S1P loading efficiency and release profile were determined using S1P competitive ELISA ($R^2$=0.970 for standard curve). As shown in FIG. 5A, the S1P loading efficiencies for PELA and C14-alkylated block copolymer meshes, determined as the percentage of S1P retained on the meshes after 5-min incubation in PBS with 0.2% FAF-BSA, were all above 90%, while the rC14-L and C6-M meshes displayed a much lower loading efficiency of 64% and 54%, respectively.

The percentages of cumulative release of S1P at various time points were determined relative to the amount retained on the respective meshes at 5 min. As shown in FIG. 5B, mesh rC14-L exhibited similar S1P early release kinetics as C6-M while meshes C14-L, C14-M shared similar profiles as that of PELA. However, in consideration of its inferior electrospinability (e.g. tendency to bead) and poor S1P loading efficiency, the random copolymer rC14-L was deemed unsuitable for S1P delivery and excluded from further investigations in the current study. Among the rest of the electrospun meshes, C6-M released significantly more S1P (~55%) than C14-block copolymer (C14-L, -M, -H) or PELA meshes (30-35%) during the first 8 h, followed by a slower yet continuing release (FIG. 5B). A total of ~80% S1P was released from C6-M, ~65% from C14-H, and ~45% from PELA and C14-M by day 7 was accomplished (FIG. 5B).

Overall, PELA, C14-L and C14-M (FIG. 5B, bar symbols) exhibited the slowest releases over 7 days, C14-H exhibited the most sustained release (FIG. 5B, square symbols), while C6-M led to a higher burst release of S1P (FIG. 5B, circle symbols). Among the alkylated copolymers well-suited for electrospinning, C14-M, C14-H and C6-M were thus chosen for further investigation as to whether/how the three distinctive release profiles may translate into differential in vitro angiogenic outcomes by tube formation assays. Given the unalkylated nature, the PELA mesh, although with similar S1P release profile as C14-M, was also included in the tube formation assay.

Tube Formation Assay

Figure 6:
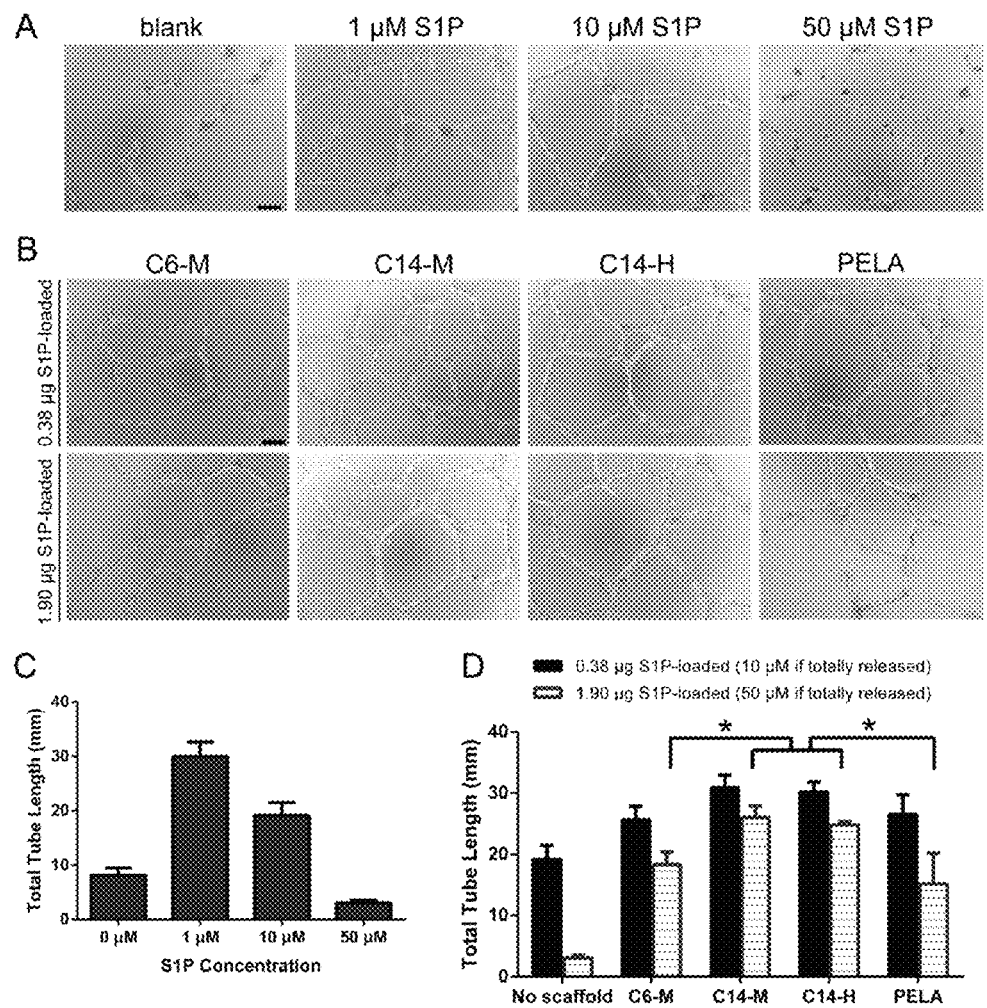
FIG. 6. Representative micrographs and total tube length quantifications (n=3-4) of HUVEC-Matrigel cultures after 17 h exposure to free S1P solutions of varying concentrations (A & C) or polymer meshes preloaded with varying doses of S1P (B & D). Scale bar=100 μm.

HUVEC tube formation assay was employed to evaluate the pro-angiogenic activity of released S1P in vitro. (Lee et al. 1999 *Biochem Biophys Res Commun* 264:743-50.) It was first showed that in the absence of a polymer carrier, the total tube length increased with the direct supplement of 1-μM S1P, however, such proangiogenic effect was compromised at the higher concentration of 10-μM S1P. Furthermore, the direct exposure of HUVEC-Matrigel culture to a very high concentration of 50-μM S1P significantly inhibited tube formation (resulted in a dramatic inhibition of cell mobility) compared to no-S1P control (FIGS. 6A and 6C).

When S1P was delivered via the amphiphilic polymer scaffolds, more robust and uniform tube formations were observed. When S1P was loaded on C14-alkylated copolymer meshes at a dose equivalent to 10-μM upon 100% release, total tube lengths observed were equivalent to that observed upon supplementation of 1-μM free S1P (FIGS. 6B and 6D). This observation supports that the amphiphilic polymer scaffolds effectively prevented the burst-release of high doses of S1P that could have been inhibitory to tube formations, with the C14-alkylated (C14-M) slightly more effective than the C6-alkylated counterpart (C6-M) or PELA. The benefit of slower and more sustained releases of S1P from C14-alkylated copolymer (C14-M & C14-H) meshes were more profoundly reflected when a higher loading dose of S1P was applied (equivalent to 50-μm S1P upon 100% release). The total tube length observed was longer than those stimulated with 10-μM free S1P. The C6-M and PELA meshes preloaded with the same high-dose S1P resulted in significantly shorter total tube lengths, although still comparable to that observed with the culture supplemented with 10-μM free S1P.

Ex-Ovo Chicken Chorioallantoic Membrane (CAM) Assay

Figure 7:
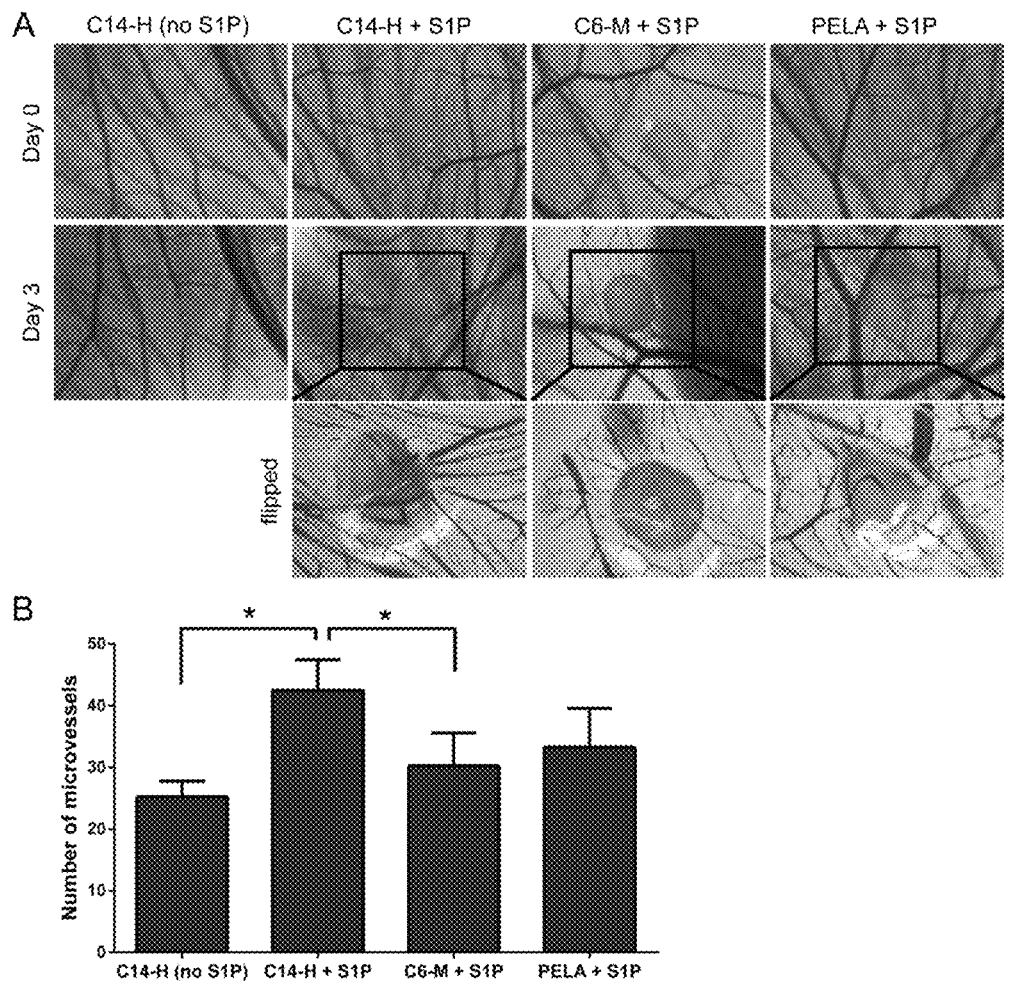
FIG. 7. Ex-ovo angiogenic effects of amphiphilic polymer meshes preloaded with 0.5-μg S1P examined by CAM assay.

To further explore the effect of S1P release kinetics on angiogenesis over a longer period (several days as opposed to 17 h in the HUVEC tube formation assay), three S1P-bearing amphiphilic groups (PELA, C6-M and C14-H) with distinct S1P release kinetics were subjected to the ex-ovo CAM assay. As representatively shown in FIG. 7A (top and middle row), the S1P-loaded C14-H group induced the most noticeable shift of surrounding vessels towards the implant. This is also accompanied by the most pronounced neovessel growth observed with the group implanted with S1P-loaded C14-H mesh, as supported by the quantification of total microvessels surrounding the implants (FIG. 7B). In comparison, S1P-bearing C6-M meshes, which led to more burst early release of S1P than C14-H, induced less potent neovessel growth (FIG. 7B). The morphologies of the neovessels beneath the meshes were more clearly visualized from the flipped CAM images (FIG. 7A, bottom row; note that the flipped image for C14-H without S1P was not shown as the CAM was damaged during the "flipping" process).

Retention/Release of Protein Therapeutics

Experiments also demonstrated that the amphiphilic polymer platform of the invention can be employed for the retention/release of protein therapeutics, for example, rhVEGF165 or rhBMP-2 (R&D systems) on alkylated amphiphilic polymers (C14-M and C14-H) vs. non-alkylated amphiphilic polymer PELA vs. hydrophobic polymer PLA.

Initial loading doses were 10-ng rhVEGF or 10-ng rhBMP-2 per mesh (6.3 mm in diameter), shown in FIG. 12 and FIG. 13, respectively. Commercial ELISA kits (R&D systems) were used for the quantification. The protein-loaded meshes were incubated in 1-mL PBS at 37° C. and retrieved at predetermined time points. The PBS was collected for ELISA while the retrieved mesh was transferred into a fresh 1-mL PBS for continued incubation up to 7 days. The cumulative protein released into the PBS was quantified by ELISA (n=3). These data show that both C14-H and C14-M exhibited outstanding retention and the slowest release of rhVEGF165 among the four, whereas C14-M and C14-H exhibited the slowest and fastest release of rhBMP-2 among the four, respectively.

Co-Delivering S1P in Combination with VEGF

Also demonstrated was the synergistic effect of co-delivering S1P in combination with VEGF in promoting tube formation of HUVECs in some dose combinations (FIG. 14).

Human umbilical vein endothelial cells (HUVECs, ATCC) were cultured on gelatin-coated plates in M199 medium with 20% fetal bovine serum (FBS), 3 ng/mL bFGF, 5 units/mL heparin and 100 U/100 μg/mL Pen/Strep at 37° C. under 5% $CO_2$. The 96-well culture plate was coated with 50 μL/well growth factor reduced Matrigel and incubated at 37° C. for 0.5 h to allow Matrigel to solidify. Then HUVECs suspended in 100 mL of M199 medium with 0.1% FBS and 100 U/100 μg/mL Pen/Strep were seeded on the Matrigel at $2\times10^4$ cells/well. The S1P and/or VEGF solutions were carefully added to each well, followed by continued incubation at 37° C. for 17 h. After removing culture media, the HUVECs were fixed with 10% formalin saline solution and imaged with an Axiovert 40 CFL microscope equipped with a QImaging camera at 25× magnifications (representatively shown in A). The total tube length in each well (n=3) was quantified by ImageJ (NIH) as shown in Figure B. All quantitative data are plotted as mean±standard derivation. Student's t-tests were employed for statistical analysis. *$P<0.05$, **$P<0.01$. These data support synergistic delivery of 10-mM S1P in combination with a lower dose of VEGF (10 ng/ml) more effectively promoted the tube formation than S1P alone, while the synergistic delivery higher dose of VEGF (50 ng/ml VEGF) in combination of this dose of S1P did not. Synergistic effect of the co-delivery of VEGF along with higher dose of S1P was not as significant.

Materials and General Instrumentation

Sphingosine-1-phosphate (S1P) was purchased from Cayman Chemical (Ann Arbor, Mich.). Growth factor reduced Matrigel was obtained from BD Biosciences (Bedford, Mass.). Fertile chicken eggs were supplied by Charles River Labs (Wilmington, Mass.). All other chemicals and reagents were purchased from Sigma-Aldrich (St. Louis, Mo.) or Fisher Scientific (Pittsburgh, Pa.) and used as received unless otherwise stated. 2-Hydroxyhexadecanoic acid was synthesized from 2-bromohexadecanoic acid per literature protocols.

NMR spectra were recorded on a Varian INOVA-400 spectrometer. Molecular weights and polydispersity of polymers were determined by gel permeation chromatography (GPC) on a Varian Prostar HPLC system equipped with two 5-mm PLGel MiniMIX-D columns and a PL-ELS2100 evaporative light scattering detector. Calibrations were performed with polystyrene standards (polymer laboratories). THF was used as the eluent at a flow rate of 0.3 mL/min.

Design Rationale of the Amphiphilic Polymers and Alkylated Lactide Monomers

PLA-PEG-PLA (PELA)-based amphiphilic copolymer-based platform is designed to enable interactions between the polar S1P headgroup and the hydrophilic PEG segment, as well as the lipophilic S1P tail with the hydrophobic PLA blocks. Alkylated polylactides to PELA was inserted either in discrete blocks between the PEG core and the PLA ends or randomly with the PLA blocks to further enhance S1P binding via hydrophobic interactions between the aliphatic side chains and the S1P lipid tail (FIG. 1A). It is worth noting that complete elimination of PLA from the amphiphilic copolymers (i.e., substituting two PLA blocks in PELA with alkylated polylactides) tended to result in copolymers with lower molecular weight liquids (Table 2) that are unsuitable for electrospinning fabrication of bulk scaffolds. Three distinct design elements were altered to allow the scaffolds to interact with S1P with varied affinities: the alkyl side chain lengths (C6 vs. C14), distribution (random copolymers with alkyl side chains spreading out vs. block copolymers with the alkyl side chains more densely clustered), and presentation density (low, medium and high alkylated repeating units relative to PEG core).

The design of 3-methyl-6-alkyl-1,4-dioxane-2,5-diones as alkylated lactide monomers was motivated by their biocompatible degradation products, a-hydroxyl fatty acids, that are present in plants and mammals. (Kishimoto et al. 1963 *J Lipid Res* 4:139-43; Foulon et al. 2005 *J Biol Chem* 280:9802-12.) The choice of mono- instead of bi-alkylated lactides was due to the concern that the excessive steric hindrance of the latter that may compromise the ring-opening polymerization efficiency.

Monomer Syntheses

3-Methyl-6-hexyl-1,4-dioxane-2,5-dione ($C_6LA$): The monomer synthesis was carried out following a protocol modified over literature. To an ice-bath chilled acetone solution (150 mL) of 2-hydroxyoctanoic acid (5.0 g, 31.21 mmol) and $Et_3N$ (8.71 mL, 62.42 mmol) was slowly added 2-bromopropionyl bromide (3.43 mL, 32.77 mmol). The white suspension was then stirred at room temperature for 0.5 h before it was filtered. The obtained white residue was further washed with acetone twice to give a combined light yellow filtrate of a total volume of 300 mL, to which was added $Et_3N$ (8.71 mL, 62.42 mmol). The mixture was stirred at 65° C. for 2 h before it was cooled to room temperature and concentrated to 50 mL under reduced pressure. The concentrate was filtered, further concentrated and diluted with a mixture of n-hexane and EtOAc (n-hexane/EtOAc=3/1, 150 mL), and passed through a short silica gel column to give the crude product, which was recrystallized twice with n-hexane to yield a white solid racemic monomer (1.85 g, 27.7% yield). $^1$H NMR (400 MHz, $CDCl_3$) δ 5.02 (m, 1H), 4.90 (m, 1H), 2.00 (m, 2H), 1.67 (m, 3H), 1.61 (m, 2H), 1.52 (m, 6H), 0.88 (m, 3H) ppm; $^{13}$C NMR (100 MHz, $CDCl_3$) δ 167.77, 167.15, 77.11, 76.03, 72.73, 72.48, 32.15, 31.68, 31.62, 30.23, 28.97, 28.74, 24.84, 24.52, 22.71, 22.68, 17.77, 16.07, 14.24, 14.21 ppm.

3-Methyl-6-tetradecyl-1,4-dioxane-2,5-dione ($C_{14}LA$): The monomer $C_{14}LA$ was prepared in a similar fashion from 2-hydroxyhexadecanoic acid instead of 2-hydroxyoctanioic acid. Recrystallized racemic product (white solid) was obtained in a 43.1% yield. $^1$H NMR (400 MHz, $CDCl_3$) δ 5.01 (m, 1H), 4.89 (m, 1H), 2.02 (m, 2H), 1.68 (m, 3H), 1.52 (m, 2H), 1.30 (m, 22H), 0.87 (t, J=6.4 Hz, 3H) ppm; $^{13}$C NMR (100 MHz, $CDCl_3$) δ 167.71, 167.08, 77.13, 76.05, 72.49, 32.15, 30.26, 29.91, 29.90, 29.88, 29.87, 29.82, 29.79, 29.71, 29.67, 29.59, 29.53, 29.47, 29.33, 29.10, 24.90, 24.59, 22.92, 17.80, 16.10, 14.36 ppm.

Polymer Syntheses

The synthesis of amphiphilic copolymers was conducted using one-pot ROP by sequential (for block copolymer) or simultaneous (for random copolymer) addition of the respective monomers. The polyethylene glycol (PEG, 20,000 Dalton) was dried by azeotropic distillation with toluene. The D,L-lactide was freshly purified by recrystallization with ethyl acetate twice. Catalyst stannous octoate, $Sn(Oct)_2$, was prepared as a stock solution in anhydrous toluene, and added in equivalent molar ratio to PEG. The feeding ratio of D,L-lactide, $C_6LA$ or $C_{14}LA$ monomers to PEG varied based on the target polymer compositions as described in Table 2 and Table 1. $^1$H NMR spectra of intermediates and crude products were taken to ensure that the monomer conversions were >90% for each step. The yields and GPC characterizations ($M_n$, PDI) of the triblock and pentablock copolymers are summarized in Table 2 and Table 1.

Pentablock copolymer $PLA_{312}$-b-$P(C_{14}LA)_{15}$-b-$PEG_{454}$-b-$P(C_{14}LA)_{15}$-b-$PLA_{312}$ (C14-L): PEG (600 mg, 0.03 mmol) and $C_{14}LA$ (300 mg, 0.92 mmol) were combined in a Schlenk vessel (10 mL), which was dried at 150° C. for 0.5 h under vacuum. After being cooled to room temperature, the reaction vessel was purged with argon, and $Sn(Oct)_2$ solution (0.03 mmol) was added and the solvent was evaporated. The mixture was heated at 150° C. for 0.5 h to allow polymerization of the alkylated lactide, followed by the addition of D,L-lactide (2700 mg, 18.73 mmol) under argon. The melt mass was allowed to polymerize at 150° C. for another 1 h before it was quenched by exposure to air at room temperature. The crude product was purified by dissolving in chloroform and precipitating in ice-cold methanol. $^1$H NMR (400 MHz, $CDCl_3$) δ 5.17 (m, 90H), 3.64 (s, 138H), 1.51 (m, 345H), 0.87 (t, J=6.80 Hz, 6H) ppm. $^{13}$C NMR (100 MHz, $CDCl_3$) δ 169.81, 169.62, 169.56, 169.52, 169.34, 70.77, 69.39, 69.20, 32.14, 29.93, 29.59, 22.91, 16.96, 16.89, 14.35 ppm.

Pentablock copolymer $PLA_{278}$-b-$P(C_{14}LA)_{31}$-b-$PEG_{454}$-b-$P(C_{14}LA)_{31}$-b-$PLA_{278}$ (C14-M): $^1$H NMR (400 MHz, $CDCl_3$) δ 5.18 (m, 38H), 3.64 (s, 66H), 1.54 (m, 179H), 0.87 (t, J=6.80 Hz, 6H) ppm. $^{13}$C NMR (100 MHz, $CDCl_3$) δ

169.81, 169.56, 169.34, 70.78, 69.39, 69.20, 32.15, 29.93, 29.59, 22.91, 16.97, 16.89, 14.35 ppm.

Pentablock copolymer $PLA_{231}$-b-$P(C_{14}LA)_{51}$-b-$PEG_{454}$-b-$P(C_{14}LA)_{51}$-b-$PLA_{231}$ (C14-H): $^1H$ NMR (400 MHz, $CDCl_3$) δ 5.17 (m, 26H), 3.63 (s, 43H), 1.54 (m, 147H), 0.87 (t, J=6.80 Hz, 6H) ppm. $^{13}C$ NMR (100 MHz, $CDCl_3$) δ 169.81, 169.56, 169.53, 169.34, 70.78, 69.39, 69.20, 32.14, 29.93, 29.89, 29.59, 22.91, 16.95, 16.89, 14.34 ppm.

Pentablock copolymer $PLA_{301}$-b-$P(C_6LA)_{31}$-b-$PEG_{454}$-b-$P(C_6LA)_{31}$-b-$PLA_{301}$ (C6-M): $^1H$ NMR (400 MHz, $CDCl_3$) δ 5.15 (m, 38H), 3.63 (s, 58H), 1.58 (m, 155H), 0.86 (t, J=6.80 Hz, 6H) ppm; $^{13}C$ NMR (100 MHz, $CDCl_3$) δ 169.83, 169.62, 169.55, 169.53, 169.34, 70.76, 69.38, 69.19, 31.70, 22.72, 16.94, 16.87, 14.23 ppm.

Random copolymer $P[LA_{312}$-$(C_{14}LA)_{15}$-$EG_{454}$-$(C_{14}LA)_{15}$-$LA_{312}]$ (rC14-L): PEG (600 mg), $C_{14}LA$ (300 mg) and D,L-lactide (2700 mg) were combined in a Schlenk vessel, and dried at 150° C. under vacuum for 0.5 h. The $Sn(Oct)_2$ solution (0.03 mmol) was then added and the solvent was evaporated. The mixture was allowed to polymerize under argon at 150° C. for 1 h. The polymerization was quenched by exposure to air at room temperature and purified by dissolving in chloroform and precipitating in ice-cold methanol. $^1H$ NMR (400 MHz, $CDCl_3$) δ 5.17 (m, 93H), 3.63 (s, 152H), 1.54 (m, 370H), 0.87 (t, J=6.80 Hz, 6H) ppm; $^{13}C$ NMR (100 MHz, $CDCl_3$) δ 169.83, 169.56, 169.35, 70.75, 69.38, 69.19, 32.12, 29.89, 29.56, 22.89, 16.95, 16.88, 14.34 ppm.

Triblock copolymer $PLA_{347}$-$PEG_{454}$-$PLA_{347}$ (PELA): PEG (1000 mg, 0.05 mmol) and D,L-lactide (5000 mg, 34.69 mmol) were combined in a Schlenk vessel and dried under vacuum for 0.5 h. The mixture was allowed to polymerize at 150° C. for 45 min, following the addition of $Sn(Oct)_2$ solution (0.05 mmol) under argon. The polymerization was quenched and the polymer was purified as described above. $^1H$ NMR (400 MHz, $CDCl_3$) δ 5.17 (m, 3.87H), 3.64 (s, 5.77H), 1.55 (m, 12H) ppm.

Differential Scanning Calorimetry (DSC) Analysis

The DSC analysis was carried out on a Q200 Modulated DSC (TA Instruments), which was calibrated with indium and sapphire standards prior to use. Under nitrogen atmosphere, each specimen (10 mg) was heated at a rate of 10.00° C./min from −90° C. to 150° C., then cooled to −90° C. at the same rate before being heated back to 150° C. Thermal transitions detected during the second heating cycle were used for data interpretation.

Mesh Fabrication by Electrospinning

The dried polymers were dispersed in a mixed solvent of chloroform and D,D-dimethylformamide (4:1 v/v) at a concentration of 25% (w/v) overnight. The polymers were electrospun into fibrous meshes by ejecting respective polymer solution through a blunt 22 gauge needle at a rate of 1.7 mL/h under 12 kV to a grounded Al-receiving plate set at 15 cm apart from the needle tip. $^1H$ NMR analysis of the mesh dissolved in $CDCl_3$ confirmed that there was no detectable residue D,D-dimethylformamide. The meshes were further dried in house vacuum overnight.

Scanning Electronic Microscopy (SEM)

The dried meshes were sputter coated with 4-nm gold and imaged on a Quanta 200 FEG MKII scanning electron microscope (FEI Inc., Hillsboro, Oreg.) under high vacuum at 5 kV. The average fiber diameter was quantified from 50 randomly selected fibers in the micrograph acquired under 1000× magnification using ImageJ (NIH).

Fabrication of Dense Polymer Films by Solvent Casting

In a typical procedure, the respective polymer (200 mg) was first dissolved in chloroform (4 mL) to obtain a clear solution, which was then cast into a 40 mm×70 mm rectangle Teflon mold. The solvent was allowed to evaporate at room temperature overnight before the casted film was further dried under house vacuum and lifted off from the mold.

Water Contact Angle Measurements

The water contact angle was determined with the sessile drop technique on a CAM 200 goniometer (KSV Instruments, Finland) connected with a charge-coupled device (CCD) camera. Deionized water droplets were deposited on the surface of electrospun or solvent-cast specimen. The contact angles from left and right side of each droplet were recorded at 30 sec following the initial water contact. Seven measurements from 3 specimens were taken for each electrospun mesh type and ten measurements were taken for each solvent-cast film.

Mesh Porosity Determination

To determine the porosity of the electrospun mesh, circular specimens of the same diameter (6.3 mm; n=3) were cut from electrospun meshes and the respective solvent-cast films using a puncher. The porosity (%) of each mesh was calculated based on its weight relative to that of the solvent-cast film, adjusted by their respective thickness measured by a digital caliper: porosity (%)=[1-(Weight$_{mesh}$×thickness$_{film}$)/(weight$_{film}$×thickness$_{mesh}$)]×100%.

S1P Loading

The electrospun meshes were punched into circles of 6.3 mm in diameter, weighed and sterilized with UV irradiation (254 nm, 1 h for each side). Fresh S1P solutions in PBS were carefully loaded onto each mesh (for S1P release study: 5 µL of 0.76-µg/µL solution to achieve 3.8-µg S1P loading per mesh; for tube formation assay: 2 or 10 µL of 0.19-µg/µL solution to achieve 0.38-µg or 1.90-µg S1P loading per mesh). The S1P-loaded meshes were incubated at 37° C. for 1 h and 4° C. for another 4 h before they were air-dried in laminar flow hood overnight.

For CAM assay, pre-hydrated meshes were lyophilized, UV-sterilized, cut into circles of 3 mm in diameter and loaded with 0.5-µg S1P (1 µL of 0.5-µg/µL S1P solution in PBS) per mesh. The S1P-loaded meshes were then incubated and air-dried as described above.

S1P Release

The S1P-loaded specimens (n=3) were placed in 200 µL of PBS solution containing 0.2% fatty acid-free-bovine serum albumin (FAF-BSA) and incubated at 37° C. with 5% $CO_2$. FAF-BSA was added to stabilize the released S1P and prevent them from aggregating to ensure their detection by ELISA. It was shown that in the absence of BSA, S1P standards became less detectable by ELISA. With the supplementation of 0.2% or 0.4% BSA, S1P standard remained consistently detected by ELISA. Thus, 0.2% FAF-BSA was chosen for the release study. At specific time points (5 min, 8 h, 1, 3, 5 and 7 days), the release solutions were collected, and fresh PBS solution with 0.2% FAF-BSA was added for continued incubation. The collected solutions were stored at −80° C. until time of quantification. The released S1P concentration was quantified using a sphingosine 1 phosphate assay kit (Echelon Biosciences, Salt Lake City, Utah) following the vendor's instruction. The S1P loading efficiency (%) was calculated as: (initial S1P loading−released S1P at 5 min)/initial S1P loading×100%

Tube Formation Assay

Human umbilical vein endothelial cells (HUVECs, ATCC, passage 6), were cultured on gelatin-coated plates in M199 medium with 20% fetal bovine serum (FBS), 3 ng/mL bFGF, 5 units/mL heparin and 100 U/100 µg/mL Pen/Strep at 37° C. under 5% $CO_2$. The 96-well culture plate was coated with 50 μL/well growth factor reduced Matrigel and incubated at 37° C. for 0.5 h to allow Matrigel to solidify. Then HUVECs suspended in 100 μL of M199 medium with 0.1% FBS and 100 U/100 μg/mL Pen/Strep were seeded on the Matrigel at $2 \times 10^4$ cells/well. After 30 min of cell attachment, PBS solutions of S1P or S1P-loaded meshes were carefully added to each well, followed by continued incubation at 37° C. for 17 h. After removing the meshes and culture media, the HUVECs were fixed with 10% formalin saline solution and imaged with an Axiovert 40 CFL microscope equipped with a QImaging camera at 25× and 100× magnifications. The total tube length in each well (n=3-4) was quantified by ImageJ (NIH).

Chicken Chorioallantoic Membrane (CAM) Assay

An ex-ovo CAM assay was used to examine the pro-angiogenic effects of S1P-loaded meshes. Briefly, fertile chicken eggs were incubated blunt side up at 37° C. in 70% humidity for 3 days, and rotated three times daily. Then the eggs were wiped with 70% ethanol, carefully cracked into 100-mm Petri dishes, and incubated for another 7 days. Sterilized circular meshes loaded with 0.5-μg S1P or PBS control were carefully placed on the CAM, and the embryos were cultured for 3 more days. The morphology of blood vessels surrounding the implants was photo-documented via a stereomicroscope by a digital camera (DFC 295, Leica) at 16× magnification. The CAM surrounding the mesh was then fixed with 10% formalin solution in PBS, flipped, and imaged at 25× magnification.

Data Analysis

All quantitative data are plotted as mean±standard derivation. Student's t-tests were employed for statistical analysis. Significance level was set as p<0.05.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. An amphiphilic degradable block copolymer, comprising the structure of

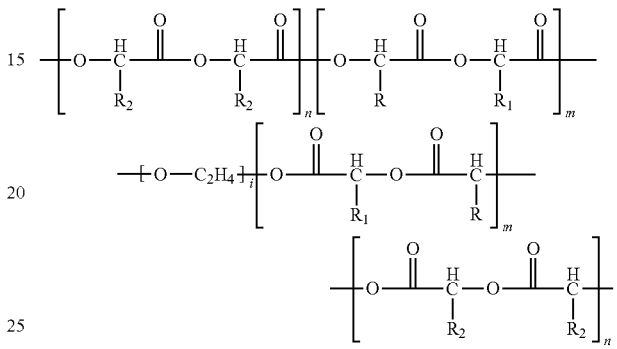

wherein
each of $R_1$ and $R_2$ is independently a $C_1$-$C_2$ alkyl group;
R is a linear alkyl chain of a length from about $C_6$ to about $C_{24}$;
i is an integer from about 10 to about 5,000;
each m is an integer from about 1 to about 1,000; and
each n is an integer from about 10 to about 5,000.

2. The amphiphilic degradable block copolymer of claim 1,
each of $R_1$ and $R_2$ is a methyl group;
R is a linear alkyl chain of a length from about $C_{12}$ to about $C_{18}$;
i is an integer from about 200 to about 800;
each m is an integer from about 10 to about 100; and
each n is an integer from about 100 to about 500.

3. The amphiphilic degradable block copolymer of claim 2, wherein the ratio of i:m:n ranges from about 1~50:1~50:1~50 to about 50~1:50~1:50~1.

4. The amphiphilic degradable block copolymer of claim 1, having a molecular weight from about 10,000 to about 1,000,000 Dalton.

5. The amphiphilic degradable block copolymer of claim 1, having a polydispersity from about 1.0 to about 2.0.

6. An amphiphilic degradable random copolymer, comprising
hydrophilic monomer units, having the structure of

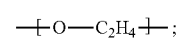

lipophilic monomer units, having the structure of

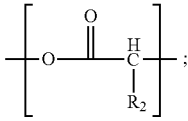

and
lipophilic monomer units, having the structure of

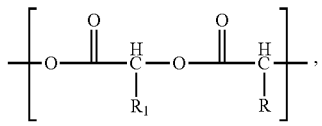

wherein
each of $R_1$ and $R_2$ is hydrogen or a $C_1$-$C_2$ alkyl group; and
R is a linear or substantially linear alkyl chain of a length from about $C_6$ to about $C_{24}$, and
the ratio of hydrophilic units:lipophilicunits:lipophilic units with alkyl chains ranges from about 1~10:1~10:1~10 to about 10~1:10~1:10~1.

7. The amphiphilic degradable random copolymer of claim 6, wherein
each of $R_1$ and $R_2$ is a methyl group; and
R is a linear alkyl chain of a length from about $C_6$ to about $C_{18}$.

8. The amphiphilic degradable random copolymer of claim 6,
wherein the ratio of hydrophilic units:lipophilicunits:lipophilic units with alkyl chains ranges from about 1~50:1~50:1~50 to about 50~1:50~1:50~1.

9. A fibrous scaffold of made from an amphiphilic degradable copolymer of claim 1, loaded with a lipid or protein, wherein the fibrous scaffold is in a form selected from electrospun fibrous meshes, dense films, porous or macroporous 3-D scaffolds and dense 3-D scaffolds.

10. The fibrous scaffold of claim 9, loaded with S1P at a loading efficiency greater than about 70%, and preferably greater than 90%.

11. The fibrous scaffold of claim 9, loaded with rhVEGF at a loading efficiency greater than about 70%, and preferably greater than 90%.

12. The fibrous scaffold of claim 9, loaded with rhBMP at a loading efficiency greater than about 70%, and preferably greater than 90%.

13. A method for sustained release of a biomolecule to an in vivo target location, comprising
providing a fibrous scaffold prepared from an amphiphilic degradable copolymer of claim 1;
loading the fibrous scaffold with the biomolecule to be delivered in vivo;
placing the loaded fibrous scaffold at the target location; and
causing sustain release of the biomolecule at the target location,
wherein the biomolecule is a lipid or a protein.

14. The method of claim 13, wherein the biomolecule is a lipid selected from S1P, ceramide, sphingosine, omega-3 fatty acids such as EPA and DHA.

15. The method of claim 13, wherein the biomolecule is a protein selected from VEGF, BMP, FGF, EGF, PDGF, IGF.

16. A fibrous scaffold of made from an amphiphilic degradable copolymer of claim 1, loaded with a lipid or protein, wherein the fibrous scaffold is in a form selected from electrospun fibrous meshes, dense films, porous or macroporous 3-D scaffolds and dense 3-D scaffolds.

17. The fibrous scaffold of claim 16, loaded with S1P, rhVEGF or rhBMP at a loading efficiency greater than about 70%.

18. A method for sustained release of a biomolecule to an in vivo target location, comprising
providing a fibrous scaffold prepared from an amphiphilic degradable copolymer of claim 1;
loading the fibrous scaffold with the biomolecule to be delivered in vivo;
placing the loaded fibrous scaffold at the target location; and
causing sustain release of the biomolecule at the target location, wherein the biomolecule is a lipid or a protein.

19. The method of claim 18, wherein the biomolecule is a lipid selected from S1P, ceramide, sphingosine, omega-3 fatty acids such as EPA and DHA.

20. The method of claim 18, wherein the biomolecule is a protein selected from VEGF, BMP, FGF, EGF, PDGF, IGF.

* * * * *